US011950944B2

(12) United States Patent
Zhou et al.

(10) Patent No.: US 11,950,944 B2
(45) Date of Patent: Apr. 9, 2024

(54) COMPACT X-RAY DEVICES, SYSTEMS, AND METHODS FOR TOMOSYNTHESIS, FLUOROSCOPY, AND STEREOTACTIC IMAGING

(71) Applicant: The University of North Carolina atChapel Hill, Chapel Hill, NC (US)

(72) Inventors: Otto Z. Zhou, Chapel Hill, NC (US); Jianping Lu, Chapel Hill, NC (US); Yueh Zenas Lee, Chapel Hill, NC (US); Christina Inscoe, Holly Springs, NC (US); Alex Billingsley, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 379 days.

(21) Appl. No.: 17/335,491

(22) Filed: Jun. 1, 2021

(65) Prior Publication Data

US 2021/0353238 A1 Nov. 18, 2021

Related U.S. Application Data

(63) Continuation of application No. PCT/US2019/064131, filed on Dec. 3, 2019.
(Continued)

(51) Int. Cl.
*A61B 6/00* (2006.01)
*H01J 35/14* (2006.01)
(Continued)

(52) U.S. Cl.
CPC .......... *A61B 6/4405* (2013.01); *A61B 6/4417* (2013.01); *A61B 6/4441* (2013.01);
(Continued)

(58) Field of Classification Search
CPC ................ A61B 6/4405; A61B 6/4417; A61B 6/4441; H01J 35/147
See application file for complete search history.

(56) References Cited

U.S. PATENT DOCUMENTS 7,826,595 B2 11/2010 Liu et al.
8,897,419 B1 * 11/2014 Jacob ...................... H05G 1/04
378/126

(Continued)

FOREIGN PATENT DOCUMENTS

EP 1016375 A1 7/2000
JP 2006 271513 A 10/2006
(Continued)

OTHER PUBLICATIONS

International Search Report and Written Opinion for Application No. PCT/US2019/064131 dated Mar. 26, 2020.
(Continued)

*Primary Examiner* — Hugh Maupin
(74) *Attorney, Agent, or Firm* — KDW FIRM PLLC

(57) ABSTRACT

Compact x-ray devices, systems, and methods for capturing in tomosynthesis, two-dimensional radiography, fluoroscopy, and stereotactic imaging modes. In some embodiments, the compact x-ray imaging system includes an x-ray source array including spatially distributed x-ray focal spots and a digital area x-ray detector. In some embodiments, the imaging system includes an electronic switching device configured to alternate the imaging mode of the system. In some embodiments, the imaging system includes a mechanical support configured to enable a position and orientation of the x-ray source array and the digital area x-ray detector to be adjusted such that both upper and lower extremities of a patient can be imaged using various imaging modes while a position of the plurality of spatially distributed x-ray focal
(Continued)

spots with respect to the digital area x-ray detector remains unchanged.

16 Claims, 14 Drawing Sheets

Related U.S. Application Data

(60) Provisional application No. 62/774,649, filed on Dec. 3, 2018.

(51) Int. Cl.
 *A61B 6/02* (2006.01)
 *H01J 35/18* (2006.01)

(52) U.S. Cl.
 CPC .............. *H01J 35/147* (2019.05); *A61B 6/022* (2013.01); *A61B 6/025* (2013.01); *H01J 35/18* (2013.01)

(56) References Cited

U.S. PATENT DOCUMENTS

| | | | | |
|---|---|---|---|---|
| 10,850,128 | B2* | 12/2020 | Hsieh | G01T 1/17 |
| 10,895,540 | B1* | 1/2021 | Gupta | A61B 6/03 |
| 11,406,332 | B2* | 8/2022 | Smith | A61B 6/5235 |
| 2009/0022264 | A1* | 1/2009 | Zhou | A61B 6/025 |
| | | | | 378/5 |
| 2009/0080602 | A1* | 3/2009 | Brooks | A61B 6/4258 |
| | | | | 378/65 |
| 2010/0290586 | A1* | 11/2010 | Friedrich | A61B 6/4014 |
| | | | | 378/65 |
| 2010/0329416 | A1* | 12/2010 | Tsujii | A61B 6/4441 |
| | | | | 378/21 |
| 2014/0226785 | A1* | 8/2014 | Stutman | A61B 6/484 |
| | | | | 378/36 |
| 2014/0241492 | A1 | 8/2014 | Tamura et al. | |
| 2014/0369459 | A1* | 12/2014 | Foos | A61B 6/03 |
| | | | | 378/4 |
| 2015/0043712 | A1* | 2/2015 | Wang | A61B 6/4021 |
| | | | | 378/42 |
| 2015/0223767 | A1 | 8/2015 | Sehnert et al. | |
| 2016/0183887 | A1 | 6/2016 | Toba | |
| 2016/0256128 | A1 | 9/2016 | Wang et al. | |
| 2017/0042489 | A1* | 2/2017 | Boyd | A61B 6/025 |
| 2017/0055929 | A1* | 3/2017 | Machida | A61B 6/5235 |
| 2020/0305809 | A1* | 10/2020 | Schwoebel | H01J 35/147 |
| 2023/0240633 | A1* | 8/2023 | Turner | A61B 6/4405 |
| | | | | 378/98 |

FOREIGN PATENT DOCUMENTS

| | | |
|---|---|---|
| JP | 2010 151726 A | 7/2010 |
| JP | 2010 240106 A | 10/2010 |
| JP | 2011 245003 A | 12/2011 |
| JP | 2016 127870 A | 7/2016 |
| JP | 2016 135319 A | 7/2016 |
| JP | 7294592 B2 | 6/2023 |

OTHER PUBLICATIONS

Liu et al. "Carbon nanotube based microfocus field emission x-ray source for microcomputed tomography", Applied Physics Letters, vol. 89, 103111 (2006).

Ottenin et al., "Evaluation of the diagnostic performance of tomosynthesis in fractures of the wrist", American Journal of Roentgenology, vol. 198, Issue. 1, pp. 180-186 (2012).

Japanese Notice of Reason for Refusal for Application No. 2021525255 dated Nov. 16, 2022.

Japanese Notice of Reasons for Refusal for Application No. 2021525255 dated Jun. 8, 2022.

* cited by examiner

COMPACT X-RAY DEVICES, SYSTEMS, AND METHODS FOR TOMOSYNTHESIS, FLUOROSCOPY, AND STEREOTACTIC IMAGING

CROSS-REFERENCE TO RELATED APPLICATIONS

This patent application is a continuation of and claims priority to PCT/US2019/064131 filed Dec. 3, 2019, which claims priority to U.S. Provisional Patent Application Ser. No. 62/774,649, filed Dec. 3, 2018, the entire disclosure of which is incorporated by reference herein.

TECHNICAL FIELD

The subject matter disclosed herein relates to x-ray imaging. More particularly, the subject matter disclosed herein relates to a compact x-ray imaging system that can perform multiple functions including digital tomosynthesis, fluoroscopy, and stereotactic imaging.

BACKGROUND

Trauma to the extremities such as the wrist, ankle, or limb is very common and affects all population groups. It constitutes a significant public health issue. Standard radiography remains the basic imaging tool. However, as a 2-dimensional (2D) imaging modality it lacks sensitivity and specificity. Misdiagnosis rates are known to be high, especially for nondisplaced fractures of the scaphoid and talus as well as erosions due to rheumatoid arthritis.

Misdiagnosis leads to over treatment and unnecessary loss of productivity and quality of life, including 6-12 weeks in a cast. Missed fractures can result in a chronic, non-healing fracture which may require surgery and/or early arthritis of the joint.

Radiographically occult fracture often stems from obscuration by adjacent anatomy. Obscuration can be reduced with three-dimensional (3D) imaging modalities. Computed tomography (CT), Magnetic Resonance Imaging (MRI), SPECT/CT, and bone scanning, are known to have better specificity and sensitivity compared to radiography, but those methods are more expensive, and often unavailable. Only 14% of urgent care centers offer CT scans, yet, 80% of urgent care centers provide fracture care. A CT scan also exposes the patient to a significantly higher radiation dose than a 2D radiograph. Bone scanning increases radiation exposure from radionuclide injection and cannot be performed until >72 hours following a fracture.

Arthritis is a disease with a high morbidity and high economic cost to society. Rheumatoid arthritis (RA), an autoimmune disease, affects up to 1.0% of the global population, with women affected more frequently than men. It is characterized by proliferative, hypervascularized synovitis, resulting in bone erosion, damage to cartilage, joint destruction, and long-term disability. Osteoarthritis (OA), a chronic, debilitating joint disease characterized by degenerative changes to the bones, cartilage, menisci, ligaments, and synovial tissue, is the fourth leading source of nonfatal health burden, accounting for 3% of total years lived with a disability.

Radiography is traditionally used for the diagnosis, staging, and follow-up of patients with arthritis and for the assessment of treatment effectiveness in individual patients. The main advantages of radiography are short examination time, low cost, and easy access. However, there are also considerable disadvantages, such as low sensitivity for the detection of bone erosions, especially in patients with early arthritis. The detectability of pathologic findings is limited by structure overlapping, because three-dimensional (3D) structure is projected into a 2D image in radiography.

Tomosynthesis is a quasi-3D imaging modality that uses a series of limited-angle projection images to produce a 3D representation of the object that was scanned. It provides depth information and removes structural overlaps at significantly reduced radiation doses and costs about the same as CT. It is now widely used clinically for breast cancer detection with significantly higher sensitivity and accuracy compared to digital mammography.

Several recent scientific studies have shown tomosynthesis is superior to x-ray radiography for orthopedic imaging. In a clinical study of 30 patients with RA, it was found that the sensitivity in the detection of bone erosions in the hand and wrist increased by roughly 20% when using tomosynthesis compared with radiography, with only a fairly small increase in radiation dose compared with radiography. For patients with early RA, the median erosion score was significantly higher with tomosynthesis than with radiography of the hand and wrist. In a separate clinical study of 100 patients with acute wrist trauma, it was found that the "diagnostic value of tomosynthesis is superior to that of standard radiography" (emphasis added). M. Ottenin, A. Jacquot, O. Grospretre, et al. "Evaluation of the diagnostic performance of tomosynthesis in fractures of the wrist", American Journal of Roentgenology, 198: 180-186 (2012).

The study further concluded that because of its low cost, very low levels of radiation required, its speed, and efficient integration into workflow, tomosynthesis has a role, along with standard radiography, in the diagnosis of fractures of the wrist. With regard to scaphoid fractures in particular, it offers more reliable diagnoses and reduces the need for other expensive imaging methods.

FIG. 1 illustrates a tomosynthesis scanner 100 that is commercially available. The example tomosynthesis scanner 100 collects the projection images needed for reconstruction by mechanically moving a large single-beam x-ray tube 110 mounted on a motorized arm 120 across a long distance while taking the x-ray exposures. Because of the tube motion, the presently available tomosynthesis scanner 100 obtains images with blurred spatial resolution, and the detection sensitivity is lower than what the modality can intrinsically provide. Furthermore, the tomosynthesis scanner 100 is large, and requires a dedicated imaging room. An example of an in-room tomosynthesis scanner is the VolumeRAD Scanner, commercially available from General Electric (GE). The device uses a rotating anode x-ray tube 110 mounted on a motorized arm 120 to scan across an angular span of about 40 degrees during which about 60 projection images are taken. An area detector, such as for example a flat panel detector, is placed behind the patient. The typical source-to-imager distance is between, and including, about 100 cm to 180 cm. C-arm and mini c-arm 2D fluoroscopy devices are used for image guidance during orthopedic operations. A fluoroscopy device uses the x-ray radiation from a single focal spot to form a 2D image. It is operated in either a continuous or pulsed mode. In the continuous fluoroscopy mode the x-ray radiation is always on and the images are typically displayed at 30 frames per second. In the pulsed fluoroscopy mode, the x-ray radiation is pulsed and the images are typically displayed at 15 frames per second. A mini c-arm device as shown, for example, in FIG. 2, has a smaller source-to-imager distance, typically in the order of about 40 cm, as compared to about 100 cm-180 cm for a regular c-arm.

An example of a commercially available mini c-arm fluoroscopy device is the Fluoroscan InSight Mini C-arm Extremities Imaging System. Mini c-arm is attractive for clinical applications for multiple reasons. It takes up less space, which is precious in overcrowded operating rooms. It is mobile and can be readily maneuvered. Furthermore, the shorter source-to-imager distance is shown to reduce the scattered radiation to the operator.

To achieve the resolution at the reduced source-to-imager distance, a mini c-arm device typically uses a micro-focus x-ray tube, operating at a low tube current. For example, the Fluoroscan InSight Mini C-arm system uses an x-ray tube with a focal spot size of about 0.045 mm, tube peak kilovoltage range of between, and including, about 40 kVp and 75 kVp, and tube current of between, and including, about 0.02 mA to 0.1 mA. It has a maximum output of about 0.1 mA at 75 kVp. The detector pixel size is about 0.075 mm×0.075 mm.

However, there is no mini c-arm imaging device today that can perform both fluoroscopy imaging and tomosynthesis imaging. Although in principle this can be achieved by mechanically rotating the x-ray tube or the x-ray tube and detector pair along the c-arm, there are several technical limitations that make this approach prohibitive. In particular, to complete the tomosynthesis scan in a clinically acceptable time and to cover a reasonable angular scan the x-ray focal spot motion blur will be an order of magnitude larger than the intrinsic focal spot size of the micro-focus x-ray tube, severely degrading the imaging quality.

SUMMARY

The subject matter of the present application discloses a compact x-ray device that can perform tomosynthesis imaging, fluoroscopy imaging, and stereotactic imaging with high resolution at the point-of-care in orthopedic and radiology clinics. Some of the intended uses of the devices disclosed hereinbelow includes, for non-limiting example, diagnostic and interventional imaging of human extremities at orthopedic and radiology clinics. It is also envisioned that the devices disclosed herein can be used for other imaging applications including veterinary imaging.

In accordance with this disclosure, systems and methods for compact x-ray imaging are provided. In one aspect, a compact x-ray imaging system is provided. In some embodiments, the compact x-ray imaging system comprises an x-ray source array comprising a plurality of spatially distributed x-ray focal spots and a digital area x-ray detector; a collimation assembly connected to an exit window of the x-ray source array configured to substantially collimate x-ray radiation generated from each of the plurality of spatially distributed x-ray focal spots to a surface of the digital area x-ray detector; an electronic switching device comprising: a high voltage power supply; a current source; a switch configured to sequentially connect the current source to a plurality of field emission cathodes of the compact x-ray imaging device, with a pre-set current value, one at a time, to produce one or more projection images for tomosynthesis reconstruction without any mechanical motion of either the x-ray source array or the digital area x-ray detector; and a trigger comprising one or more first processors and/or circuitry configured to synchronize detector data collection with x-ray exposure from the plurality of spatially distributed x-ray focal spots; and a mechanical support configured to enable a position and orientation of the x-ray source array and the digital area x-ray detector to be adjusted such that both upper and lower extremities of a patient can be imaged using tomosynthesis in either non-load bearing or load bearing positions; wherein the compact x-ray imaging system is configured to operate in a plurality of imaging modes.

In some embodiments, the compact x-ray imaging system is configured to be operated either in a tomosynthesis imaging mode or a pulsed fluoroscopy mode.

In some embodiments, the compact x-ray imaging system is configured such that when the x-ray imaging device is operated in the tomosynthesis imaging mode, a scanning x-ray beam is produced by sequentially activating x-ray beams from the plurality of spatially distributed x-ray focal spots electronically without moving either the x-ray source array, the digital area x-ray detector, or the patient, in order to collect one or more required projection images for tomosynthesis reconstruction; and configured such that when the x-ray imaging device is operated in the pulsed fluoroscopy imaging mode, x-ray radiation generated from a central focal spot of the plurality of spatially distributed x-ray focal spots is pulsed from about 5 to 30 pulses per second, and for each x-ray pulse an image of an object being scanned is formed and displayed to produce an x-ray movie of the object.

In some embodiments, the compact x-ray imaging system is configured to be operated in a stereotactic mode.

In some embodiments, the compact x-ray imaging system is configured such that when the x-ray imaging device is operated in the stereotactic mode, two discrete focal spots of the plurality of spatially distributed x-ray focal spots are activated to emit x-ray radiation causing two projection images to be formed and displayed from two different angles In another aspect, a method of x-ray imaging using a compact x-ray imaging device is provided. In some embodiments, the method comprises: providing an x-ray source array with a plurality of spatially distributed x-ray focal spots, and a digital area x-ray detector; substantially collimating x-ray radiation generated from each of the plurality of spatially distributed x-ray focal spots to a surface of the digital area x-ray detector using a collimation assembly connected to an exit window of the x-ray source array; providing an electronic switching device comprising: a high voltage power supply; a current source; a switch; and a trigger comprising one or more first processors and/or circuitry; positioning and orienting the x-ray source array and the digital area x-ray detector to be adjusted such that both upper and lower extremities of a patient can be imaged using tomosynthesis in either non-load bearing or load bearing positions, while a position of the plurality of spatially distributed x-ray focal spots with respect to the digital area x-ray detector remains unchanged; sequentially connecting the current source to a plurality of field emission cathodes of the compact x-ray imaging device, with a pre-set current value, one at a time, to produce one or more projection images for tomosynthesis reconstruction without any mechanical motion of either the x-ray source array or the digital area x-ray detector; and synchronizing detector data collection with x-ray exposure from the plurality of spatially distributed x-ray focal spots; wherein the compact x-ray imaging system is configured to operate in a plurality of imaging modes.

In another aspect, a mini c-arm x-ray imaging system is provided. In some embodiments, the mini c-arm x-ray imaging system comprises a carbon nanotube based micro-focus x-ray source array comprising a plurality of spatially distributed micro-focus x-ray focal spots and a digital area x-ray detector mounted on a mini c-arm; a collimation assembly connected to an exit window of the micro-focus x-ray source array configured to substantially collimate the x-ray radiation generated from each of the plurality of spatially distributed micro-focus x-ray focal spots to a surface of the digital area x-ray detector; and an electronic switching device comprising: a high voltage power supply; a current source; a switch configured to sequentially connect the current source to a plurality of field emission cathodes of the mini c-arm x-ray imaging device with a pre-set current value, one at a time, to produce one or more projection images for tomosynthesis reconstruction without any mechanical motion of either the micro-focus x-ray source array or the digital area x-ray detector; and a trigger comprising one or more processors and/or circuitry configured to synchronize detector data collection with x-ray exposure from the plurality of spatially distributed micro-focus x-ray focal spots; wherein the mini c-arm x-ray device is configured to operate in either a three-dimensional tomosynthesis imaging mode, a fluoroscopy mode, or a stereotactic mode.

In another aspect, a method of x-ray imaging using a mini c-arm x-ray imaging system is provided. In some embodiments, the method comprises: providing a mini c-arm x-ray imaging system with a carbon nanotube based micro-focus x-ray source array with a plurality of spatially distributed micro-focus x-ray focal spots, and a digital area x-ray detector mounted on a mini c-arm; substantially collimating x-ray radiation generated from each of the plurality of spatially distributed micro-focus x-ray focal spots to a surface of the digital area x-ray detector using a collimation assembly connected to an exit window of the micro-focus x-ray source array; providing an electronic switching device comprising: a high voltage power supply; a current source; a switch; and a trigger comprising one or more processors and/or circuitry; sequentially connecting the current source to a plurality of field emission cathodes of the mini c-arm x-ray imaging device with a pre-set current value, one at a time, to produce one or more projection images for tomosynthesis reconstruction without any mechanical motion of either the micro-focus x-ray source array or the digital area x-ray detector; and synchronizing detector data collection with x-ray exposure from the plurality of spatially distributed micro-focus x-ray focal spots; wherein the mini c-arm x-ray device is configured to operate in either a three-dimensional tomosynthesis imaging mode, a fluoroscopy mode, or a stereotactic mode.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which.

DETAILED DESCRIPTION

The subject matter of the present disclosure includes compact x-ray devices for imaging at, for non-limiting example, the point-of-care. The devices disclosed herein can be utilized for multiple functions. They can be used for diagnostic tomosynthesis imaging, serving a similar function as the large in-room tomosynthesis devices, but with a smaller foot print (i.e. taking up less physical space in the exam/operating rooms). The devices of the present disclosure can also be used for interventional purposes, providing image guidance for surgery and other procedures. In some embodiments, the devices can be used either in the tomosynthesis imaging mode, 2D radiography mode, fluoroscopy mode, or stereotactic mode.

Figure 1:
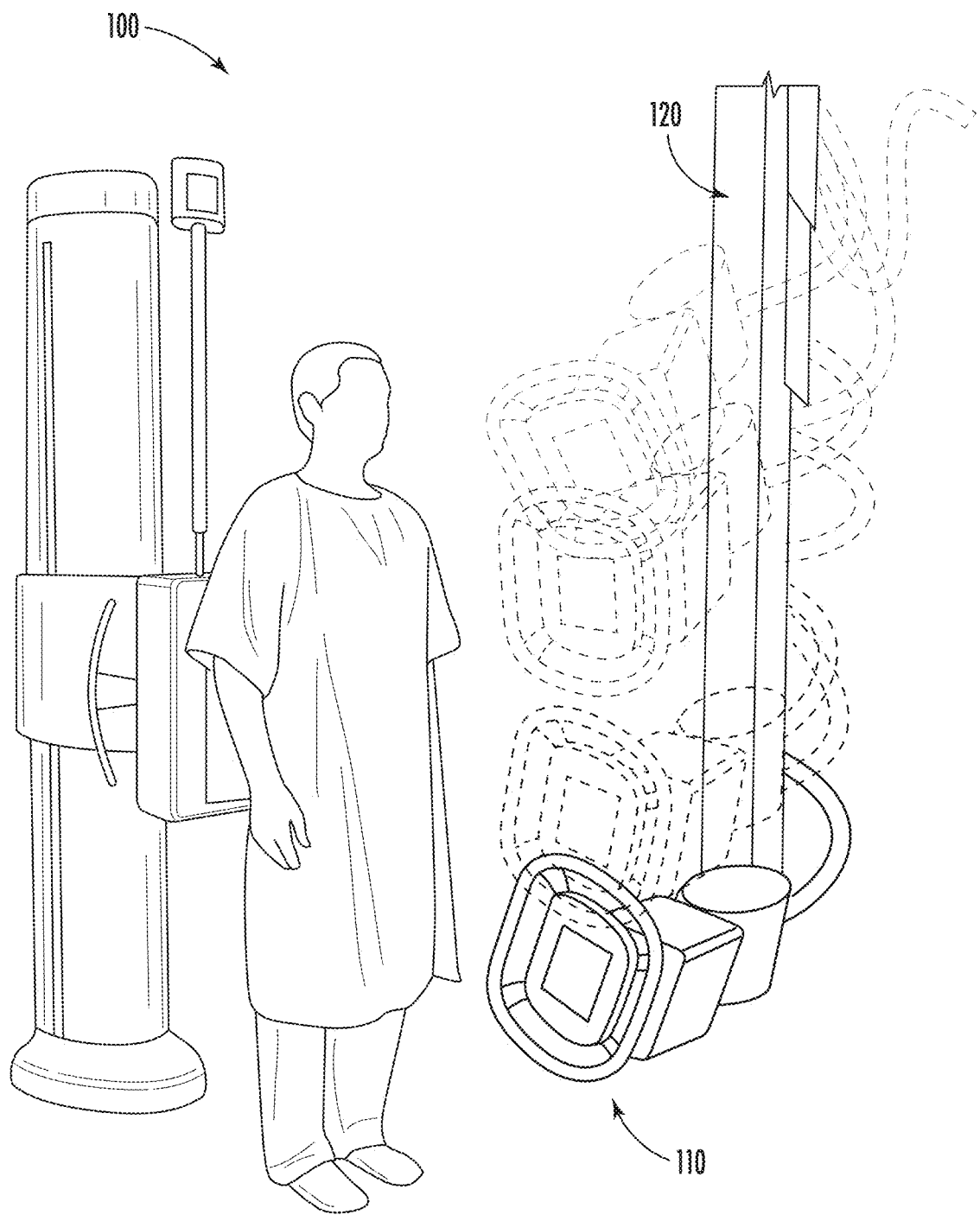
FIG. 1 is an illustration of a traditional tomosynthesis scanner that is commercially available.
Figure 2:
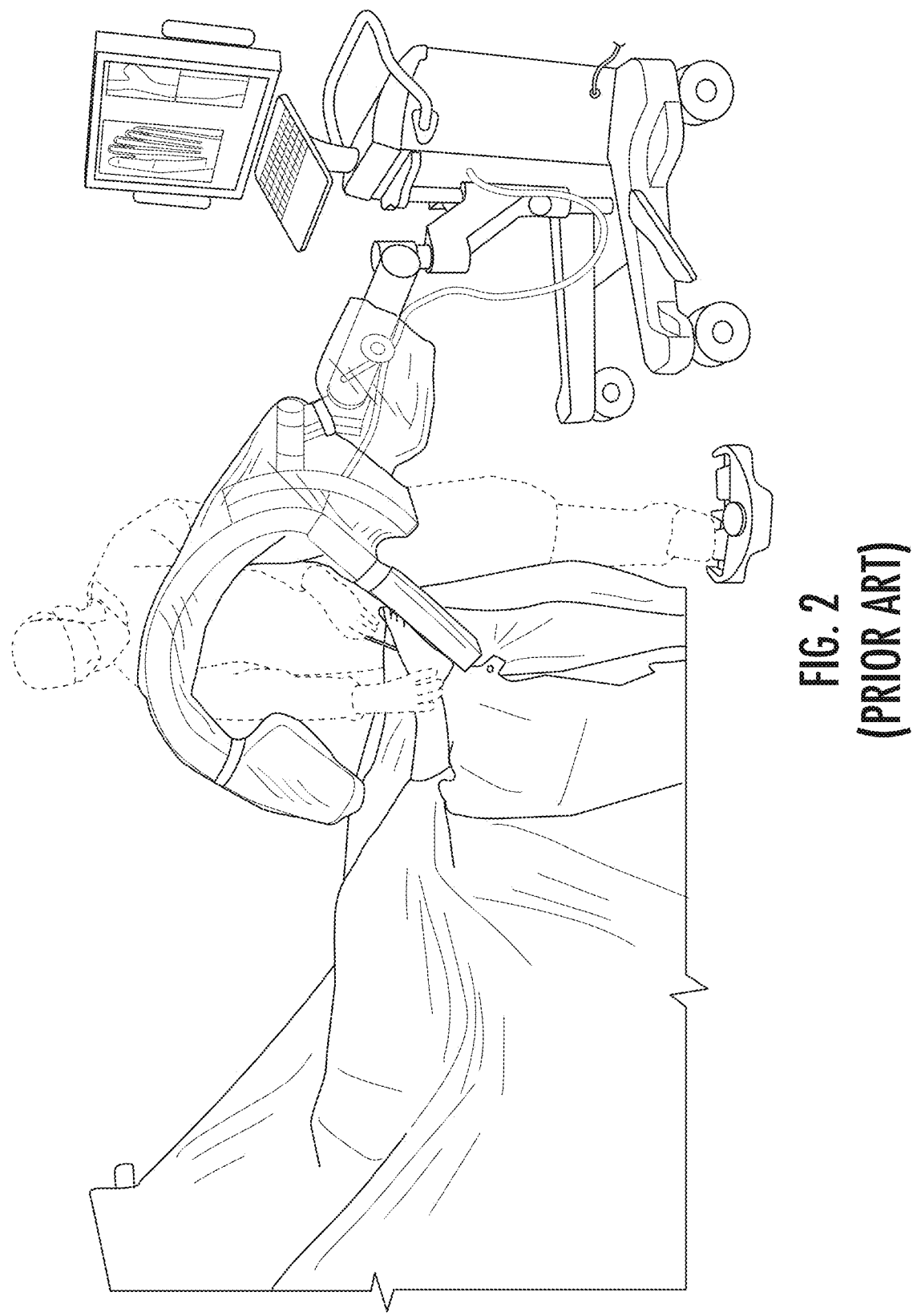
FIG. 2 is an illustration of a traditional mini c-arm x-ray imaging device according to devices commercially available.
Figure 3A:
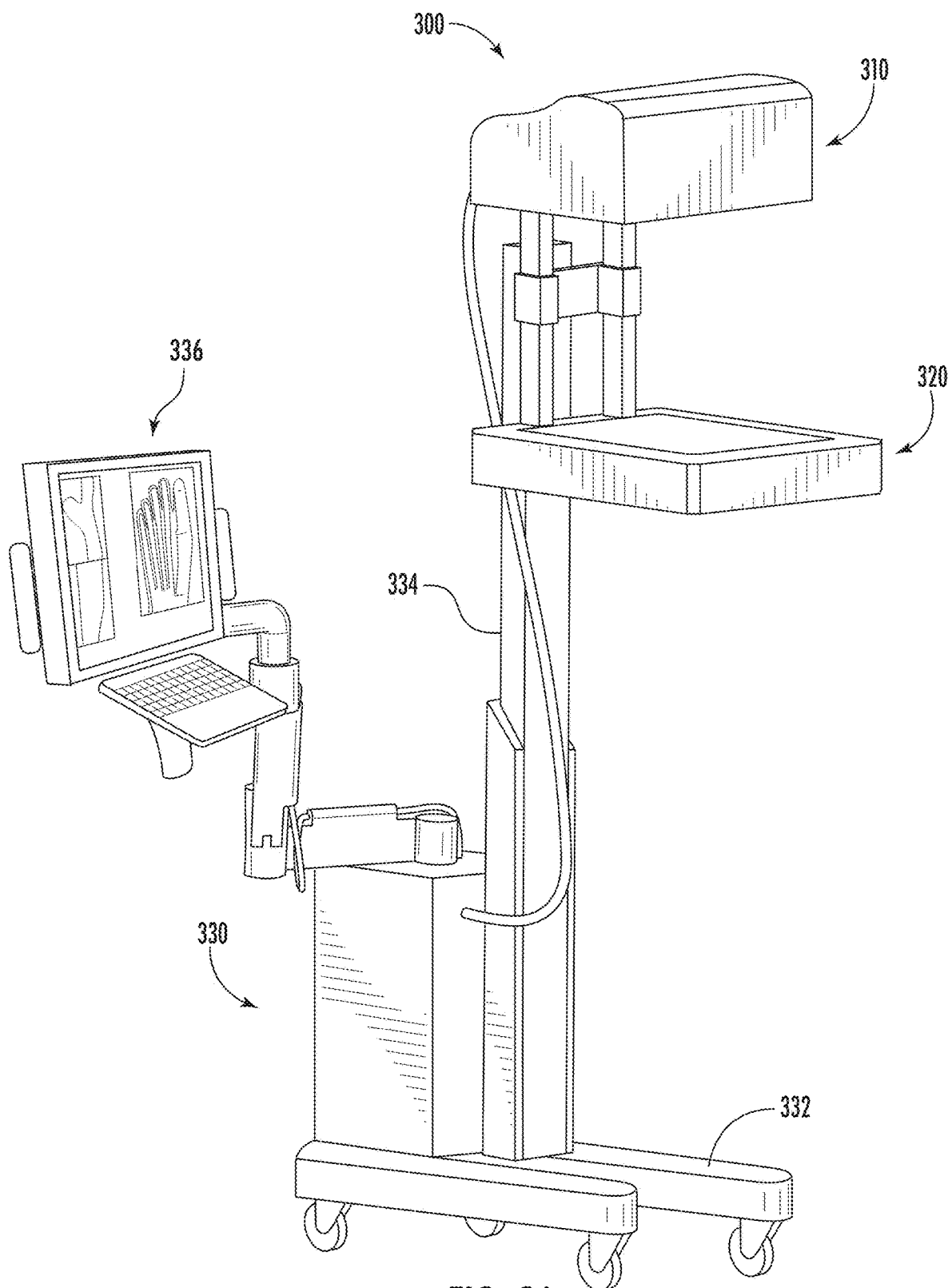
FIG. 3A, FIG. 3B, FIG. 3C, FIG. 3D are illustrations of example x-ray imaging systems according to some embodiments of the present disclosure.

FIG. 3A illustrates one possible embodiment of the subject matter disclosed herein. In some embodiments, the x-ray imaging device 300 as illustrated in FIG. 3, is a compact x-ray tomosynthesis device, comprising an x-ray source array 310 comprising a plurality of spatially distributed x-ray focal spots (not shown in this view), and a digital area x-ray detector 320. In some embodiments, the digital area x-ray detector 320 is positioned opposite and parallel to the x-ray source array 310 in order to, for non-limiting example, record the images. In some embodiments, the x-ray imaging device 300 comprises a beam limiting device or collimation assembly (not shown in this view) connected to an exit window of the x-ray source array 310. In some embodiments the collimation assembly is configured to substantially collimate x-ray radiation generated from each of the plurality of spatially distributed x-ray focal spots to a surface of the digital area x-ray detector 320. In some embodiments, the digital area x-ray detector 320 can be, for example and without limitation, a flat panel type area detector.

In some embodiments, the plurality of spatially distributed x-ray focal spots comprises two spatially distributed x-ray focal spots, or more than two spatially distributed x-ray focal spots. In some embodiments, each of the plurality of spatially distributed x-ray focal spots is microfocused with a spot size of between, and including, about 0.01 mm and 0.3 mm. For example and without limitation, in some embodiments, the spot size of each of the focal spots can be between, and including, about 0.1 mm to 0.2 mm. For example and without limitation, in some embodiments, the spot size of each of the focal spots can be about 0.1 mm. In some embodiments, at least one of the plurality of spatially distributed x-ray focal spots is micro-focused with a spot size of between, and including, about 0.01 mm and 0.3 mm. In some embodiments, the plurality of spatially distributed x-ray focal spots is positioned in a plane which is substantially perpendicular to a plane in which the digital area x-ray detector 320 is positioned. In some embodiments, the plurality of spatially distributed focal spots of the x-ray source array is positioned in a plane which is substantially parallel to a plane in which the digital area x-ray detector 320 is positioned.

To generate a scanning x-ray beam electronically, in some embodiments, the x-ray imaging device 300 further comprises an electronic switching device 330 which comprises: a high voltage power supply, a current source, and a switch. In some embodiments, the high voltage power supply and the current source are configured to supply power to the x-ray imaging device 300, including to the x-ray source array 310. In some embodiments, the switch is configured to sequentially connect the current source to one or a plurality of field emission cathodes of the x-ray source array 310. In some embodiments, the current source is sequentially connected to one or a plurality of the field emission cathodes of the x-ray source array 310, one at a time, with a pre-set current value of between, and including, about 0.05 mA and 20 mA, to produce one or more projection images for tomosynthesis reconstruction without any mechanical motion of either the x-ray source array 310 or the digital area x-ray detector 320.

In some embodiments, the electronic switching device 330 further comprises a trigger or triggering mechanism to synchronize detector data collection with the x-ray exposure from the plurality of spatially distributed x-ray focal spots. In some embodiments, the trigger can comprise, for non-limiting example, one or more first processors and/or circuitry configured to synchronize detector data collection with x-ray exposure from the plurality of spatially distributed x-ray focal spots. In some embodiments, the electronic switching device 330 is configured to operate the high voltage power supply at more than one energy level during a single imaging sequence such that projection images obtained at different anode energy levels can be combined to produce contrast enhanced 2D radiographic images and/or 3D tomosynthesis images.

In some embodiments, the x-ray imaging device 300 can be mounted on or affixed to a mobile cart 332. In some further embodiments, the x-ray imaging device 300 can comprise a mechanical support 334 configured to alter a position and orientation of the x-ray source array 310 and the digital area x-ray detector 320 to be adjustable such that, for non-limiting example, both upper and lower extremities of a patient can be imaged using tomosynthesis in either non-load bearing or load bearing positions. In some embodiments, the imaging can occur while a position of the plurality of spatially distributed x-ray focal spots remains unchanged with respect to the digital area x-ray detector 320. In some embodiments, the x-ray imaging device 300 of the present disclosure is configured to be operated in either a tomosynthesis imaging mode, a pulsed fluoroscopy mode, or a stereotactic mode.

In some embodiments, the x-ray imaging device 300 comprises one or more central processors configured to switch between imaging modes. In some embodiments, the central processor can be embedded within or be a part of, or otherwise control the electronic switching device 330. For example and without limitation, the x-ray imaging device 300 can comprise a processor that, either automatically or after receiving some input from a user, switches the imaging mode and controls the x-ray source array 310 and digital area x-ray detector 320 and various other devices in the x-ray imaging device 300. In some embodiments, the central processor is configured to switch the imaging mode between a tomosynthesis imaging mode, 2D radiography mode, fluoroscopy mode, or stereotactic mode. In this regard, the central processor can be configured to control the x-ray source array 310 and digital area x-ray detector 320 and various other devices in accordance with the description herein.

In some embodiments, when the x-ray imaging device 300 is operated in the tomosynthesis imaging mode, a scanning x-ray beam is produced by sequentially and electronically activating the x-ray beams from the plurality of spatially distributed x-ray focal spots, without moving either the x-ray source array 310, the digital area x-ray detector 320, or the patient (not shown in this view), to collect all of the projection images needed for tomosynthesis reconstruction. In one embodiment, this is accomplished by connecting the current source of the electronic switching device 330 with the field emission cathodes in the x-ray source array 310 with a pre-set current value, one at a time, to generate x-ray radiation from the plurality of spatially distributed x-ray focal spots to produce the projection images. In some embodiments, the pre-set current value is set to between, and including, about 0.05 mA and 20 mA.

Figure 3B:
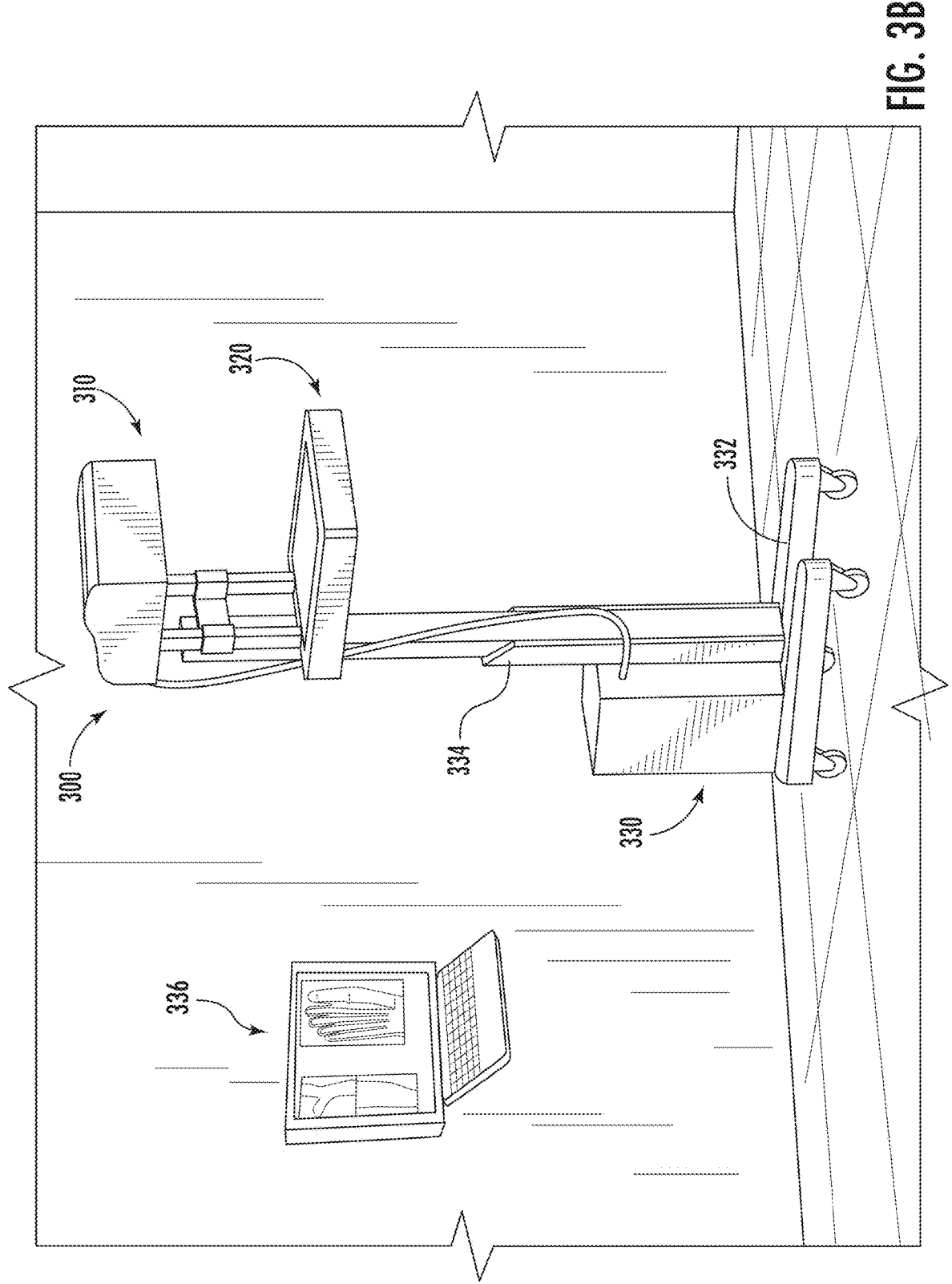
Figure 3C:
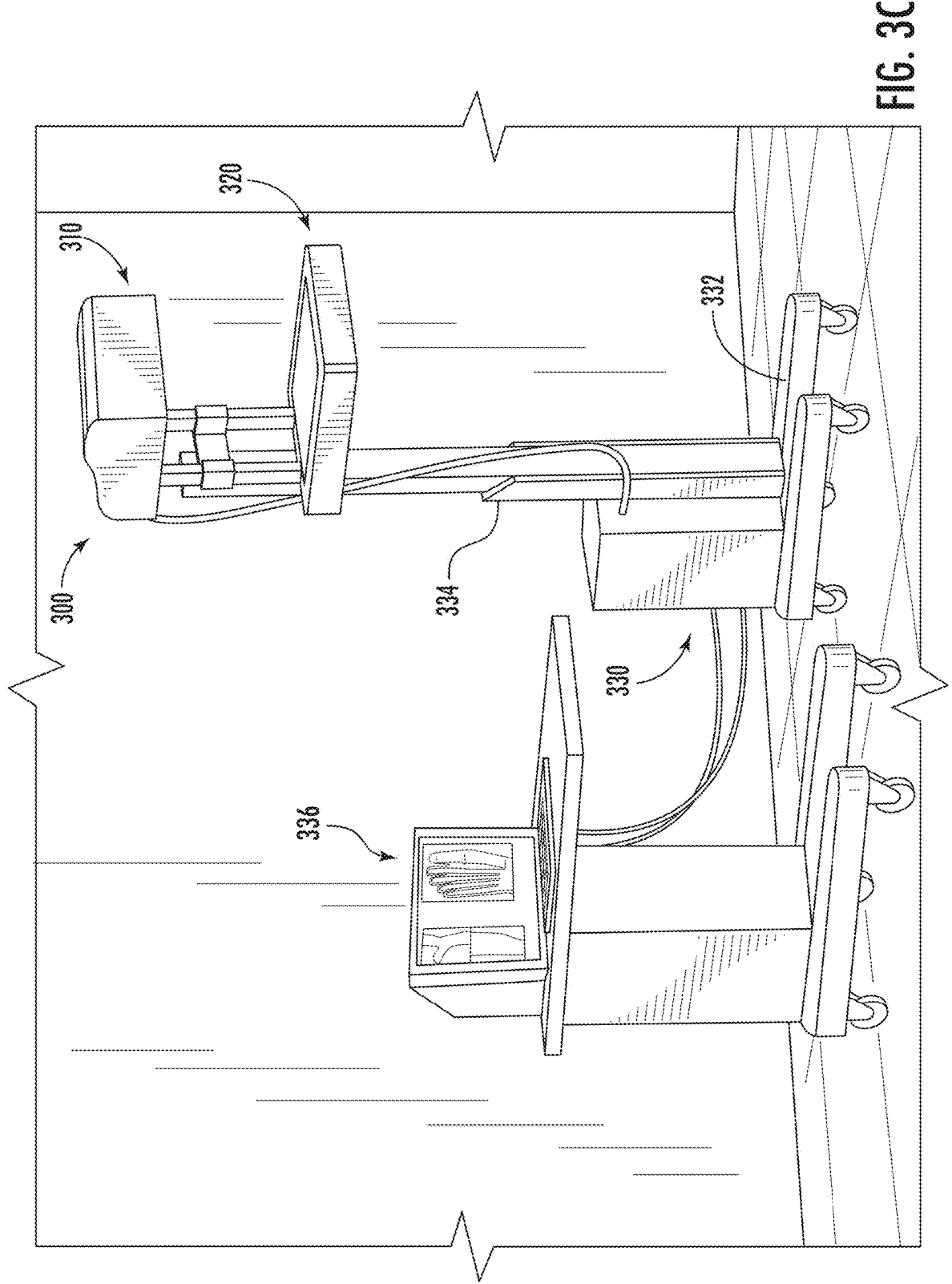

In some embodiments, the x-ray imaging device 300 further comprises one or more second processors, non-transitory computer readable medium, and a tomosynthesis image reconstruction algorithm configured to reconstruct the projection images into a stack of tomosynthesis images. In some embodiments, the x-ray imaging device 300 further comprises a viewing screen, such as monitor 336, or other display that allows a user or practitioner to view the images generated by the x-ray imaging device. In some embodiments, the x-ray imaging device 300 comprises a graphics processing unit (GPU) in order to, for example and without limitation, increase the speed of the tomosynthesis reconstruction. In some embodiments, the x-ray imaging device 300 comprises a display, such as monitor 336, or other screen separate from the main machine, for non-limiting example, mounted to a wall, as illustrated in FIG. 3B, or on a separate mobile cart, as illustrated in FIG. 3C.

Referring to FIG. 3A, in some embodiments, when the x-ray imaging device 300 is operated in the 2D radiography mode, x-ray radiation generated from one or more of the plurality of spatially distributed x-ray focal spots is used to generate a single two-dimensional x-ray image or one or more two-dimensional fluoroscopy images.

In some embodiments, when the x-ray imaging device 300 is operated in the fluoroscopy imaging mode, preferably a pulsed fluoroscopy mode, x-ray radiation generated from one of the plurality of spatially distributed x-ray focal spots, is used to generate multiple images. In some embodiments, the x-ray imaging device 300 is configured to pulse radiation sourced from the one x-ray focal spot. In some embodiments, a central x-ray focal spot of the plurality of spatially distributed x-ray focal spots is utilized and a radiation beam is pulsed using the central focal spot. In some embodiments, the one x-ray focal spot is pulsed at a rate ranging from about 5 to 30 pulses per second. In some embodiments, the central x-ray focal spot is pulsed at a pulse rate ranging from about 5 to 30 pulses per second. In some embodiments, for each x-ray pulse (with respect to either the central x-ray focal spot or another single x-ray focal spot) an image of a scanned object is formed and displayed to produce an x-ray movie or x-ray video of the scanned object.

In some embodiments, when the x-ray imaging device 300 is operated in the stereotactic imaging mode, x-ray radiation from a plurality of discrete focal spots of the plurality of spatially distributed x-ray focal spots is used to form a plurality of projection images from a plurality of different view angles and displayed. In some embodiments, the stereotactic imaging mode uses two discrete focal spots of the plurality of spatially distributed x-ray focal spots to form two projection images from two different view angles and displayed. In some embodiments, no mechanical movement of the x-ray source array 310 is required. In some embodiments, images generated when the x-ray imaging device 300 is operated in the stereotactic imaging mode, can be, for example without limitation, two-dimensional or three-dimensional images.

Figure 4A:
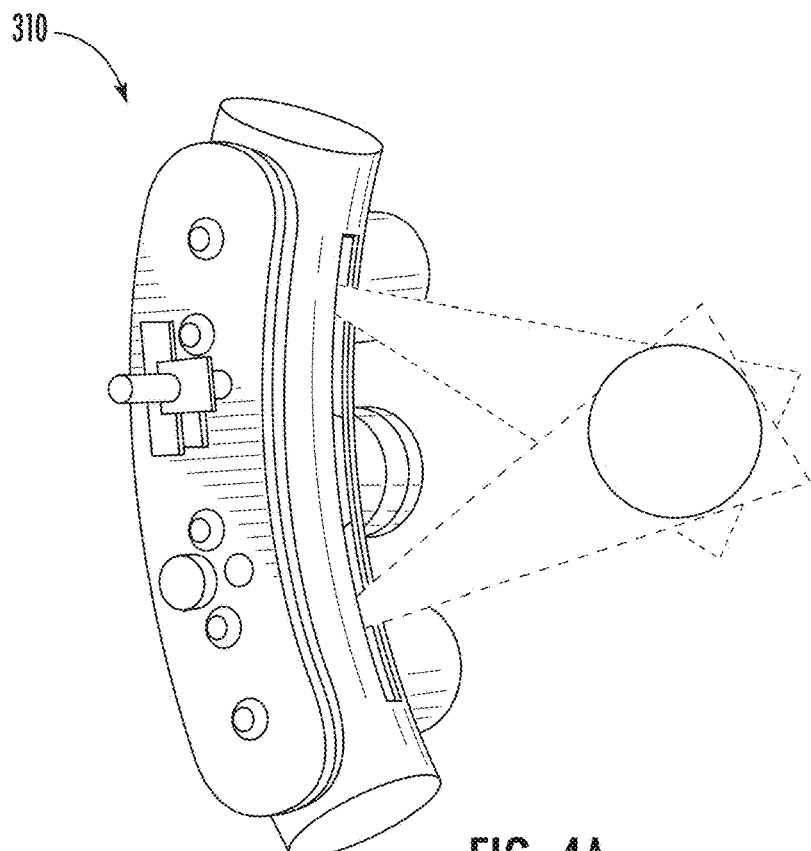
FIG. 4A and FIG. 4B are illustrations of a curved carbon nanotube (CNT) x-ray source and a linear-shaped CNT x-ray source.
Figure 4B:
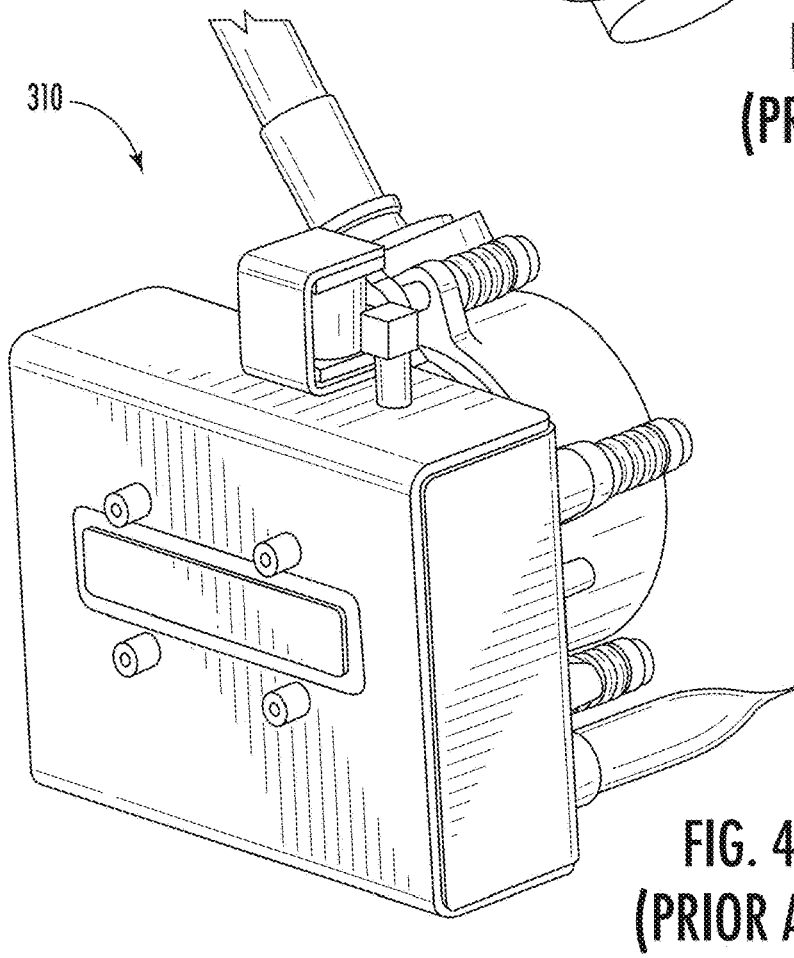

In some embodiments of the present disclosure, the x-ray source array 310 is a carbon nanotube (CNT) based x-ray array. A CNT x-ray source array utilizes an array of individually controllable CNT field emitters to generate electrons at room temperature, wherein the electrons are accelerated to bombard the anode to produce x-rays. In some embodiments of the present disclosure, the CNT field emitters are connected to the electronic switching device 330. By electronically switching the individual CNT cathodes on and off, a scanning x-ray beam can be produced from different viewing angles to collect a plurality of projection images needed for tomosynthesis reconstruction, without any mechanical motion. FIG. 4A illustrates an x-ray source operating using this principle. In some embodiments, the CNT x-ray source array 310 can be arranged in a curved fashion, such as shown in, for example and without limitation, FIG. 4A. However, in some embodiments the CNT x-ray source array 310 does not have to be shaped in a curved manner but can be straight or linear. Such a straight or linearly shaped CNT x-ray source array 310 is illustrated in FIG. 4B. Furthermore, both of the CNT x-ray source arrays 310 described in FIG. 4A and FIG. 4B are commercially available, for example and without limitation, from XinRay Systems, LLC.

With CNTs, electrons are produced at room temperature using field emission. By applying an electrical potential difference across a very sharp object, electrons may be produced at the tip of the sharp object. One requirement of x-ray imaging with modern x-ray tubes and CNTs includes focusing of each of the electron sources. With CNTs, the field emission electrons are already partially focused during the emission process, and thus, smaller focusing structures are also needed. In 2002, Zhou and colleagues demonstrated that CNTs could serve as effective field emitters for x-ray sources, due to their atomically sharp tips and high mechanical stability. Furthermore, the turn on voltages required are significantly reduced in contrast to attempts with prior diamond and tungsten tips. The CNT x-ray sources can be positioned in close proximity, allowing the creation of multi-beam x-ray sources for a variety of applications.

Figure 3D:
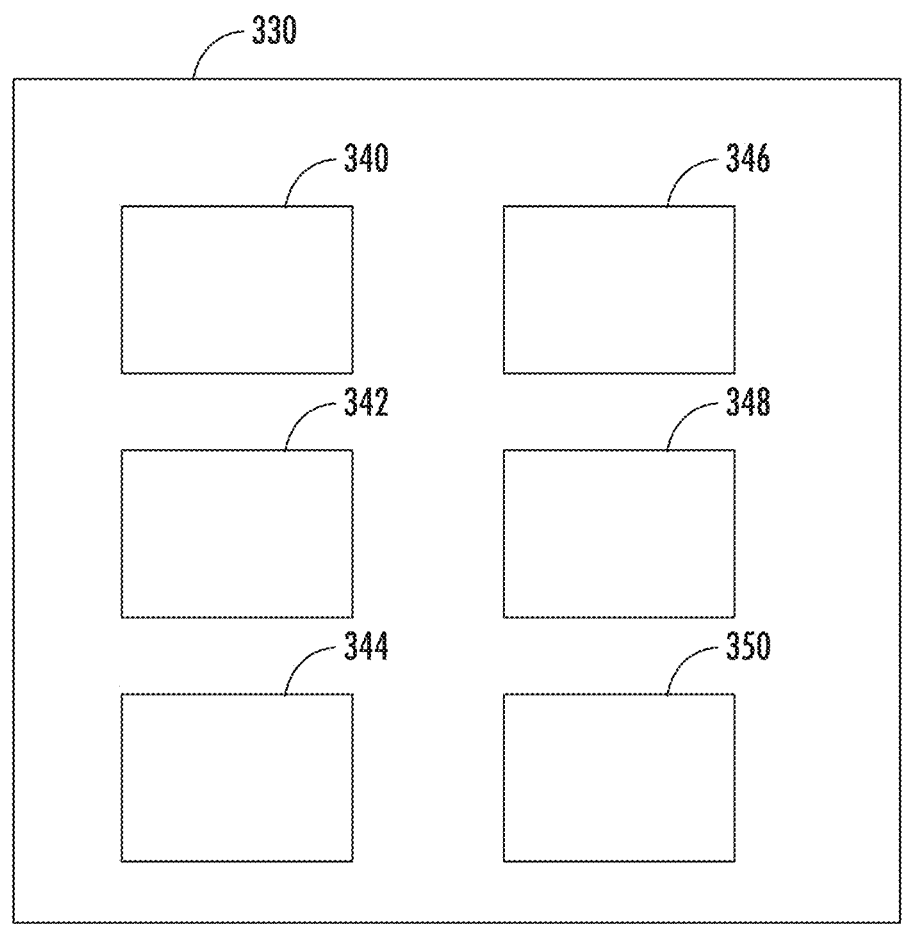

In some embodiments, the x-ray imaging device 300 of the present disclosure comprises between, and including, about five and sixty individually controllable CNT emitters as electron sources. In some embodiments, the x-ray source array has a unipolar design. In some embodiments, the anode voltage of the x-ray source array has an anode voltage between, and including, about 0 kV and 120 kV and an x-ray tube current between, and including, about 0.05 mA and 20 mA. In some embodiments, the x-ray focal spots have a spatial distribution in a line, circle, 2D array, or any other 2D or 3D geometrical configuration FIG. 3D illustrates a more detailed example of the electronic switching device 330. In some embodiments, as described herein, the electronic switching device 330 can comprise a high voltage power supply 340, a current source 342, a switch 344, a trigger comprising one or more first processors 346, one or more second processors 348, and a central processor 350. In some embodiments, the high voltage power supply 340 is configured to provide electrical power to the various components of the x-ray imaging device 300 of the present disclosure, including, for example and without limitation, the x-ray source array 310 and the digital area x-ray detector 320. In some embodiments, the current source 342 is configured to be connected, by the switch 344, to a plurality of field emission cathodes of the compact x-ray imaging device, with a pre-set current value, one at a time, to produce one or more projection images for tomosynthesis reconstruction without any mechanical motion of either the x-ray source array 310 or the digital area x-ray detector 320.

In some embodiments, the switch 344 is configured to connect the current source 342 as described herein. In some embodiments, the trigger comprising one or more first processors 346 is configured to synchronize detector data collection with x-ray exposure from the plurality of spatially distributed x-ray focal spots. In some embodiments, the one or more first processors 346 can be located in the electronic switching device 330 or in any other suitable part of the x-ray imaging device 300 as described herein. In some embodiments, the one or more second processors 348 comprise a non-transitory computer readable medium, and a tomosynthesis image reconstruction algorithm configured to reconstruct the projection images into a stack of tomosynthesis images. In some embodiments, the one or more second processors 348 is configured to automatically register non load-bearing images and load-bearing images to produce load-induced structural deformation/displacement of an extremity of a patient. In some embodiments, the one or more second processors 348 is configured to automatically register pre-contrast agent injection images and post-contrast agent injection images to produce contrast agent enhanced images of an extremity of a patient.

In some embodiments, the central processor 350 is configured to switch the x-ray imaging device 300 between imaging modes. In some embodiments, the central processor 350 can comprise a processor that, either automatically or after receiving some input from a user, switches the imaging mode and controls the x-ray source array 310 and digital area x-ray detector 320 and various other devices in the x-ray imaging device 300. In some embodiments, the central processor is configured to switch the imaging mode between a tomosynthesis imaging mode, 2D radiography mode, fluoroscopy mode, or stereotactic mode. In this regard, the central processor can be configured to control the x-ray source array 310 and digital area x-ray detector 320 and various other devices in accordance with the description herein. In some embodiments, the central processor 350 can interface or communicate with the one or more first processors 346, one or more second processors 348, or any of the other various components to receive data to either display or output on the monitor 336 or other device. For example and without limitation, the one or more second processors 348 can be configured to process and reconstruct the tomosynthesis images and send them to the central processor 350 which is configured to display the images on the monitor 336. Furthermore, in some embodiments, the detector 320 and any of the processors of the x-ray imaging device 300 may send captured images (using any imaging mode) and send to the central processor 350 for displaying on the monitor 336.

Figure 5:
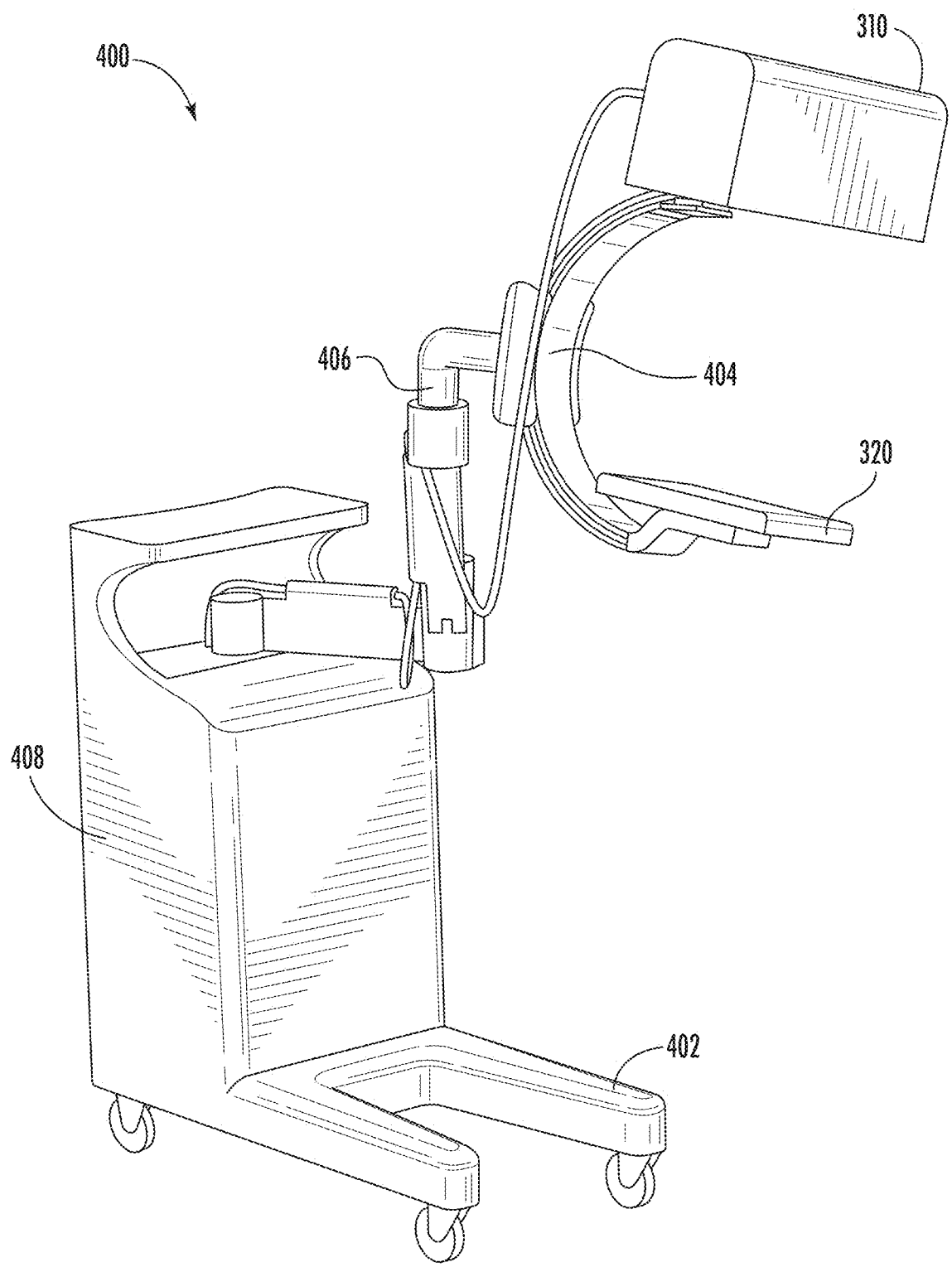
FIG. 5 is an illustration of a mobile mini c-arm x-ray imaging system according to some embodiments of the present disclosure.

FIG. 5 illustrates another embodiment of the mini c-arm x-ray imaging device 400 of the present disclosure, including a mechanical support structure that enables the position and orientation of the x-ray source and detector pair as a whole to be adjusted such that, for example and without limitation, both upper and lower extremities can be imaged in either non-load bearing or load bearing positions. The mini c-arm x-ray imaging device 400 of FIG. 5 can comprise many of the same electronic components of the previous x-ray imaging devices discussed above, including processors, switching devices, monitors, etc. In some embodiments of the present disclosure, the mechanical support is a mini c-arm 404 that is commercially used, for example without limitation, for fluoroscopy. In some embodiments the mechanical support can comprise or include a mechanized arm or other mechanized structure. In some embodiments the mechanical support can be a non-mechanized arm or other non-mechanized structure. In some embodiments, the mechanical support can be a movable support arm like that shown in FIG. 5.

In some embodiments the mechanical support can comprise a min c-arm 404 connected to an adjustable extendable support arm 406 attached to or mounted to a support structure, such as, for example and without limitation, mobile cart 402 or other mobile or non-mobile apparatus. In some embodiments, the adjustable extendable support arm 406 is configured to extend and collapse and/or swivel such that a user of the x-ray imaging device 400 can move the x-ray source array 310 and the digital area x-ray detector 320 to access a portion of a patient's body for imaging. In some embodiments, one or more second processors of the mini c-arm x-ray imaging device 400 is configured to automatically register non load-bearing images and load-bearing images to produce load-induced structural deformation/displacement of an extremity of a patient. In some embodiments, the one or more second processors is configured to automatically register pre-contrast agent injection images and post-contrast agent injection images to produce contrast agent enhanced images of an extremity of a patient.

One or more processors of the mini c-arm x-ray imaging device 400, such as the first processor, second processor, and/or central processor can all be positioned in any suitable place on the mini c-arm x-ray imaging device 400, including in the housing 408, which can also comprise an electronic switching unit as described above with respect to FIG. 3.

In some embodiments, the mini c-arm x-ray imaging device 400 of FIG. 5 comprises a carbon nanotube based micro-focus x-ray source array with a plurality of spatially distributed micro-focus x-ray focal spots, and a digital area x-ray detector mounted on a mini c-arm. Furthermore, the mini c-arm x-ray imaging device of FIG. 5 is configured to operate in either a 3D tomosynthesis imaging mode, a fluoroscopy mode, and/or a stereotactic mode as described herein. In some embodiments, the mini c-arm x-ray imaging device 400 comprises a central processor that is configured to control an electronic switching unit that switches between the various imaging modes as discussed herein.

Figure 6:
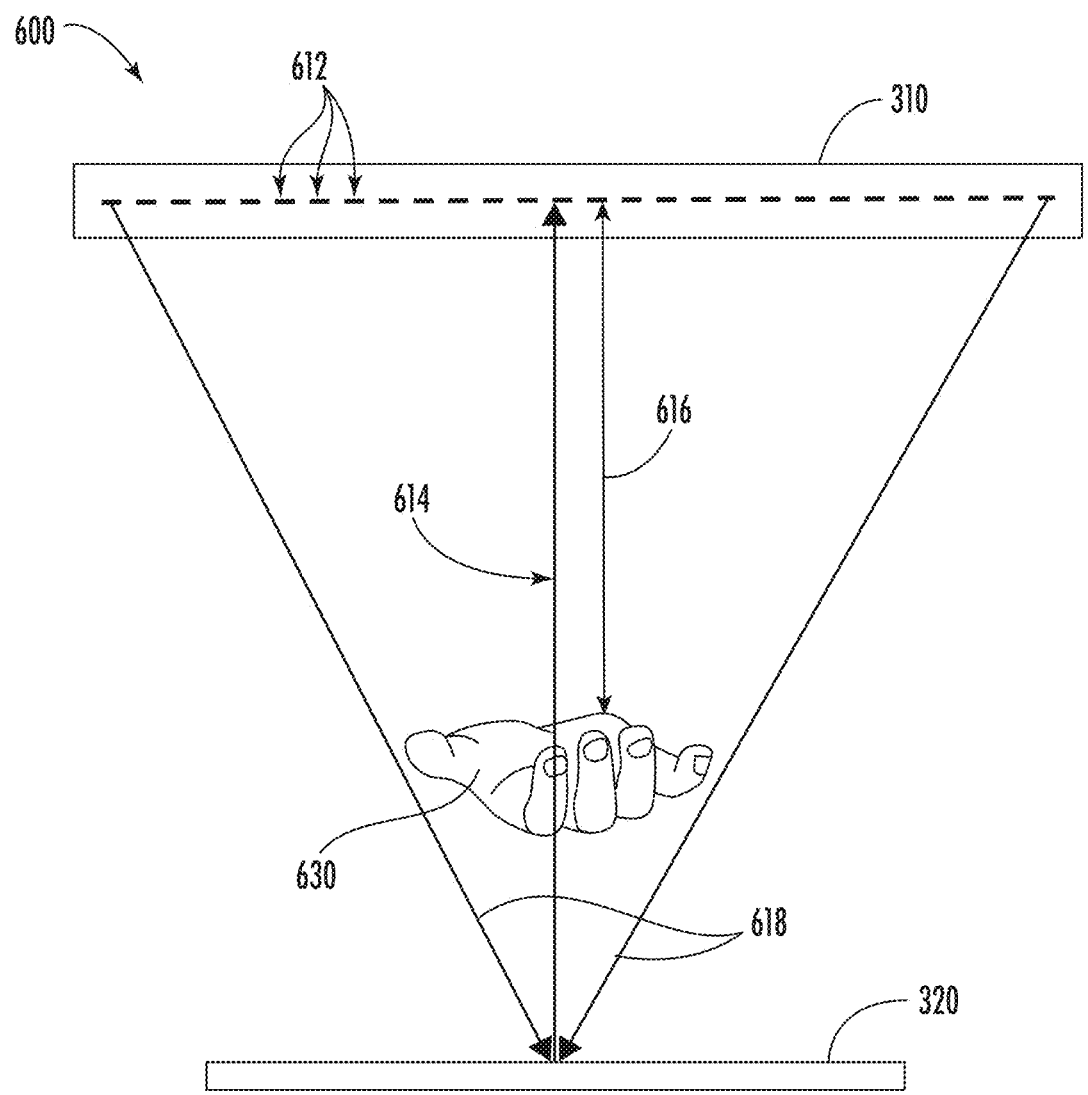
FIG. 6 and FIG. 7 are illustrations of example arrangements of various components of an x-ray imaging system according to some embodiments of the present disclosure.

The geometric arrangement 600 of some embodiments of the x-ray imaging device is illustrated in FIG. 6 with an x-ray source array 310 and a digital area x-ray detector 320 in a parallel geometry with respect to one another. To reduce the size of the imaging device, in some embodiments, the system source-to-imager-distance (SID) 614, can be between, and including, about 40 cm and 60 cm, similar to that used in the mini c-arm devices. Reducing the SID 614 also has the benefits of: a) reducing the x-ray tube power needed for the exposure; b) reducing the radiation exposure to the operator; and c) reducing the size and weight of the imaging system. Reducing the SID 614, however, has an adverse effect on the system resolution. The spatial resolution of the imaging system is determined by factors including the focal spot size of the x-ray source array 310, the pixel size of the digital area x-ray detector 320, and the magnification factor. The magnification factor is the ratio of the SID 614 over source-to-object-distance (SOD) 616, the source being the x-ray source array 310 and the object being object 630 being scanned.

To achieve the high spatial resolution needed for diagnosis imaging at different magnification factors, in one embodiment of the present disclosure, a micro-focus x-ray source array 310 is utilized. In some embodiments, for example without limitation, the source array is a CNT based micro-focus x-ray source array. In some embodiments, the sizes of the x-ray focal spots 612 in the x-ray source array 310 (for clarity, only 3 of the focal spots are marked by arrows) are preferably about 0.1 mm or less. To obtain the depth resolution, the angular scan 618 covered by the x-ray source array 310 in some embodiments is between, and including, about 10 and 50 degrees. In some embodiments, the angular scan (i.e., angular coverage) 618 of the x-ray source array 310 is about 40 degrees and the SID 616 is about 40 cm. In some embodiments, in the case of a linear x-ray source array, this would require the line formed by the x-ray focal spots 612 to be equal to about 2*tan (20 degrees)*40 cm or about 29 cm.

In some embodiments of the present disclosure, the x-ray source array 310 comprises between, and including, about 10 and 40 cathodes, wherein each cathode generates one x-ray beam from a corresponding focal spot 612 on the anode with a defined focal spot size, providing between, and including, about 10 and 40 micro-focused focal spots 612. In some embodiments, the CNT x-ray source array 310 comprises about 30 spatially distributed micro-focused x-ray focal spots 612, wherein each focal spot 612 has an average focal spot size of, for example, about 0.1 mm in full-width-at-half-maximum (FWHM). In some embodiments, the x-ray source array 310 operates in an energy range of between, and including, about 0 kVp and 120 kVp. In one embodiment, the x-ray source array 310 operates in an energy range of between, and including, about 40 kVp and 80 kVp in order to image, for non-limiting example, extremities.

In some embodiments, the CNT based micro-focused x-ray source array 310 uses an electrostatic focusing structure to focus the electron beam for a small area on the x-ray anode. One non-limiting example of an electrostatic focusing structure is the Einzel type electrostatic focusing lens. The construction of a single-beam CNT micro-focus x-ray tube with Einzel type electrostatic focusing lens is described in the publication "Carbon nanotube based microfocus field emission x-ray source for microcomputed tomography", Appl. Phys. Lett. 89, 103111 (2006); Zejian Liu et al. and U.S. Pat. No. 7,826,595, the disclosures of which are incorporated herein by reference in their entirety.

In some embodiments, an x-ray photon output from the x-ray source array 310 depends on the x-ray focal spot 612 size. Reduction of focal spot 612 size limits the maximum tube power, and therefore limits the amount of x-ray fluence generated. For a micro-focused x-ray source with a stationary anode, the x-ray tube current is commonly less than 1 mA when the x-ray tube voltage is at about 70 kVp and when the x-ray focal spot 612 size is less than 0.1 mm.

For x-ray imaging, the image quality, particularly the image signal-to-noise ratio (SNR), depends on the amount of x-ray photons received by the x-ray detector 320, which depends on the entrance dose. For tomosynthesis imaging of a human wrist, a total entrance dose of between about 0.2 mGy and 0.3 mGy is commonly used in the published literature. An experiment from a CNT x-ray source array according to the present disclosure designed for dental imaging shows that the x-ray radiation production rate is about 0.4 mGy/mAs at a 40 cm SID 614 and an x-ray tube voltage of about 70 kVp. At an x-ray tube voltage of about 50 kVp, the rate is expected to reduce to 0.2 mGy/mAs. Therefore, with a 40 cm SID device, for human wrist imaging at 50 kVp, the source current needed is about 1 mA. Assuming a micro-focused source array operated at 50 kVp and 0.5 mA tube current, then the total x-ray exposure needed would be 2 seconds for the 1 mAs dose. If there are 20 projection images and the detector frame rate is 4 frames-per-second, the total detector readout time is 5 seconds, and the total scan time of the example device would be 7 seconds for the tomosynthesis imaging of a human wrist. In comparison, the current commercial in-room digital tomosynthesis scanner from General Electric takes about 10 seconds for a tomosynthesis scan. This shows that the example device of the present disclosure can perform a tomosynthesis scan with a similar, if not significantly shorter, time when compared to the large in-room scanners currently available.

Figure 7:
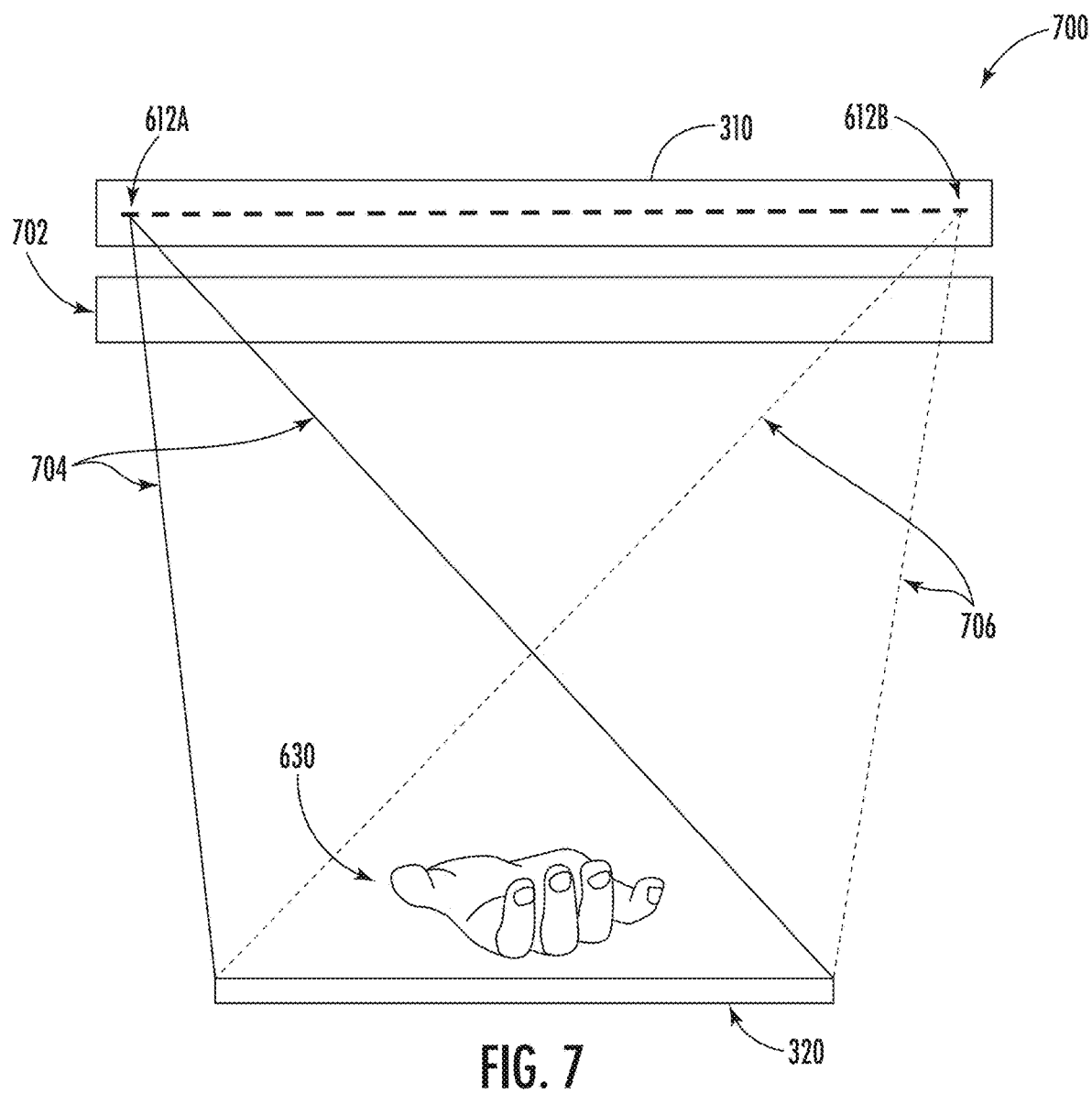

In some embodiments of the present disclosure, as illustrated in FIG. 7, the x-ray imaging device 300 can comprise a beam limiting device such as collimation assembly 702 that is configured to confine the x-ray radiation from every x-ray focal spot to the digital area x-ray detector 320 surface as required by the IEC standard. In some embodiments, the collimation assembly 702 can be, for example and without limitation, one or more collimators. In some embodiments, the collimation assembly 702 is connected to an exit window of the x-ray source array 310 and is configured to substantially collimate or confine the x-ray radiation generated from each and every one of the plurality of spatially distributed focal spots 612 to the surface of the digital area x-ray detector 320.

In some embodiments, the collimation assembly 702 comprises a primary collimator and a secondary collimator, wherein the primary collimator comprises a plurality of apertures and each aperture of the plurality of apertures is configured to allow radiation from one corresponding x-ray focal spot 612A to pass through. In other words, in some embodiments, a first aperture is fixed to or aligned with a single corresponding x-ray focal spot 612A and the first aperture is configured to allow radiation through from only that corresponding x-ray focal spot 612A. Although the apertures are not seen in this view of FIG. 7, lines 704 and 706 illustrate how radiation from each x-ray focal spot 612A and 612B, respectively, is collimated and focused on the digital x-ray detector 320.

Figure 8:
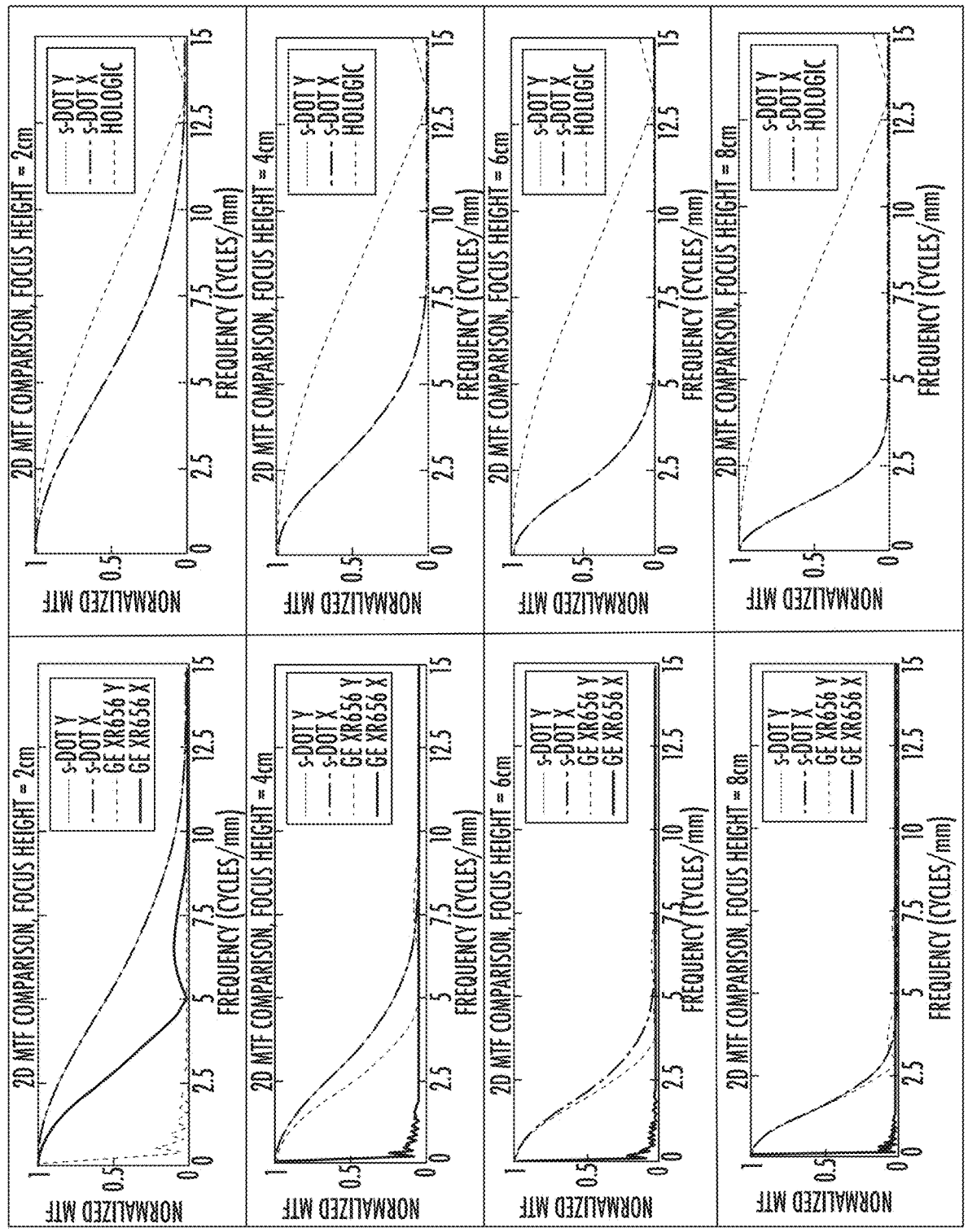
FIG. 8 illustrates simulations performed to demonstrate a system resolution of an example x-ray imaging system of some embodiments of the present disclosure.

FIG. 8 includes several graphs illustrating simulations performed to show a system resolution of an example x-ray imaging device of the present disclosure. The simulations were run to demonstrate the system resolution with the x-ray sources at different distances away from the x-ray detectors.

Figure 9:
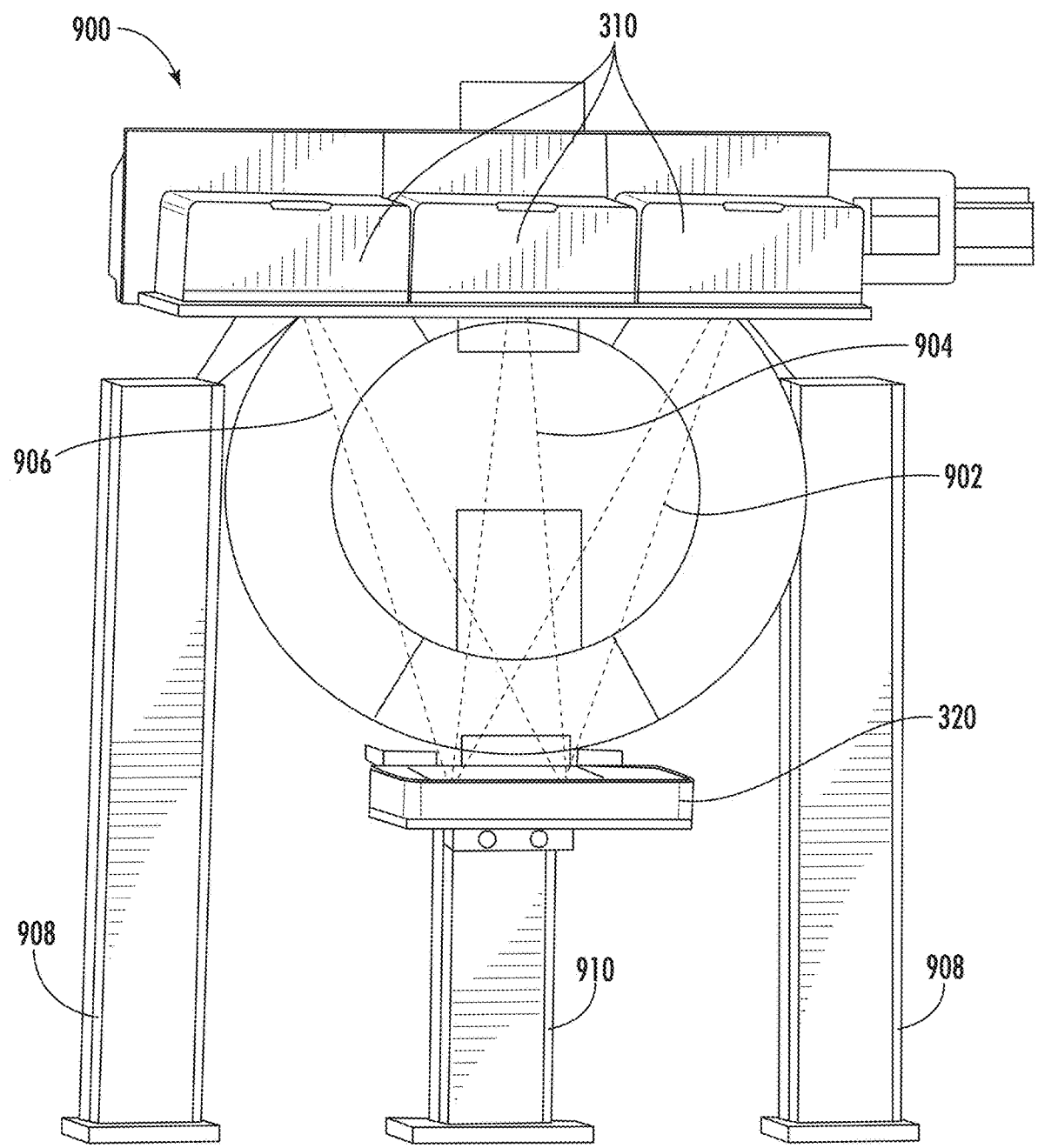
FIG. 9 is an illustration of an example benchtop x-ray imaging system according to another embodiment of the present disclosure.

The feasibility of the operation of the devices disclosed herein above was demonstrated using a bench-top device such as the bench-top device 900 shown in FIG. 9. A pre-existing short CNT x-ray source array 310 and a flat panel detector 320 were mounted on a mechanical stand 910. Additionally, the bench-top device 900 includes a set of legs 908 used to further support the bench-top device 900. The source array was translated to a total of 3 positions to cover 40 degrees at a 40 cm SID. Lines 902, 904, and 906 illustrate the angles of the x-ray beams as they were propagated towards the detector 320. Cadaver specimens were imaged at 55 kVp using 21 projections. The images were reconstructed using an iterative algorithm.

Figure 10B:
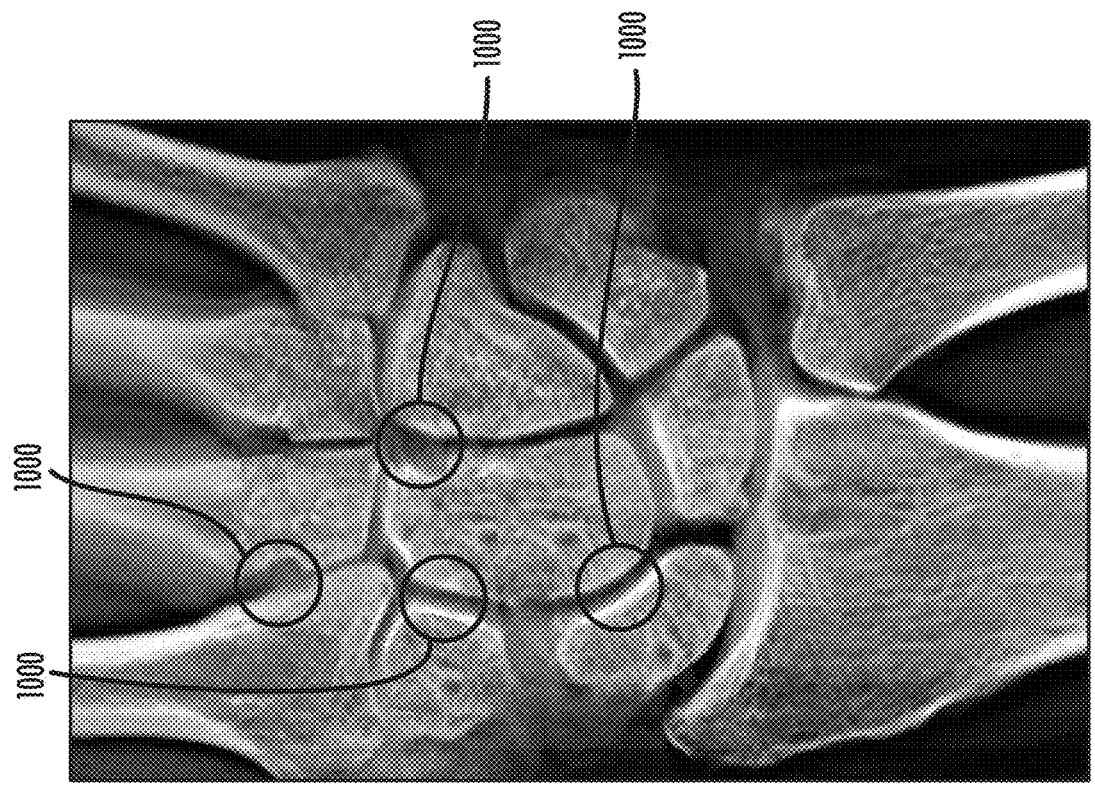
FIG. 10B illustrates a reconstruction slice image captured by a device of the present disclosure.
Figure 10A:
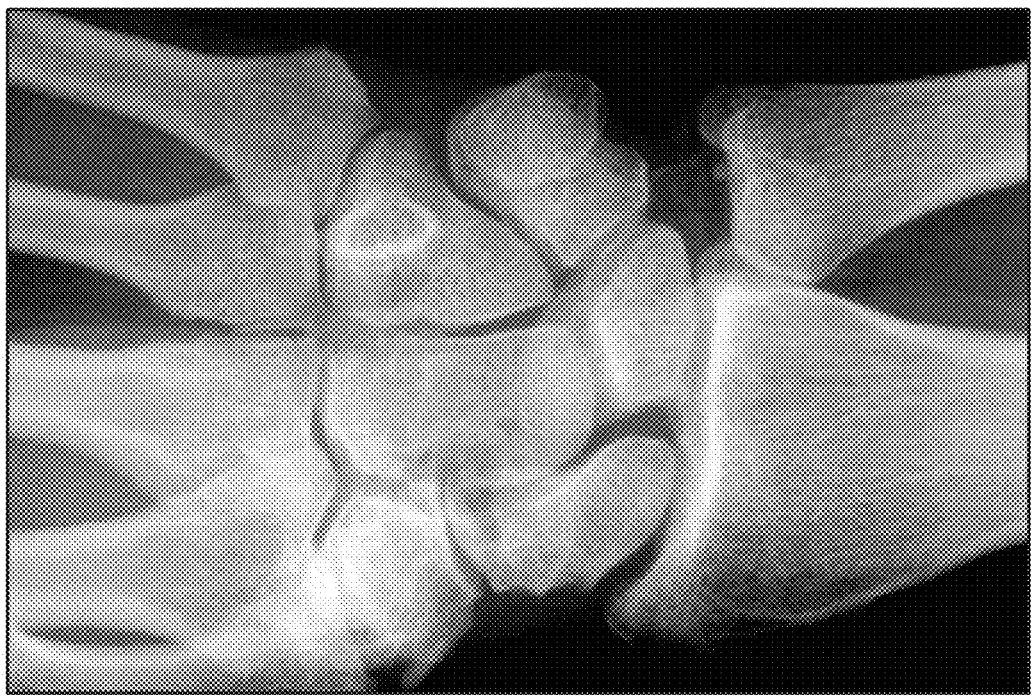
FIG. 10A illustrates an example projection image captured by traditional imaging systems that do not capture the same detail as the systems and devices according to some embodiments of the present disclosure.

Example images reconstructed by the bench-top device (or other devices according to the disclosure herein) are illustrated in FIG. 10B. FIG. 10A illustrates an example projection image of the cadaver wrist that was captured using a different device than that of the present disclosure. It was captured using conventional methods. When an observer compares the image in FIG. 10A to the image in FIG. 10B (captured using a method of the present disclosure) it is apparent that conventional methods (i.e. methods used to capture FIG. 10A) do not achieve the clarity and detail of the reconstruction slice image in FIG. 10B (created by the device of the present disclosure). As pointed out by the reference indicators, the reconstruction slice image in FIG. 10B is able to capture the joint spaces and lesions 1000 that are not visible on the projection images in FIG. 10A.

Figure 11B:
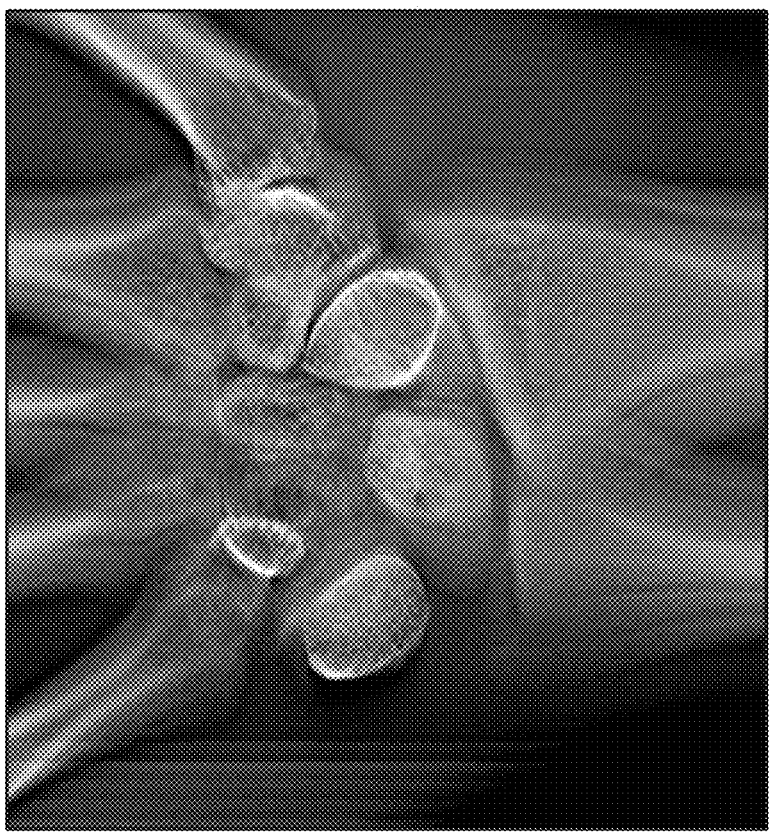
FIG. 11A and FIG. 11B illustrate example tomosynthesis reconstruction slice images captured at different aspects by an example system of the present disclosure.
Figure 11A:
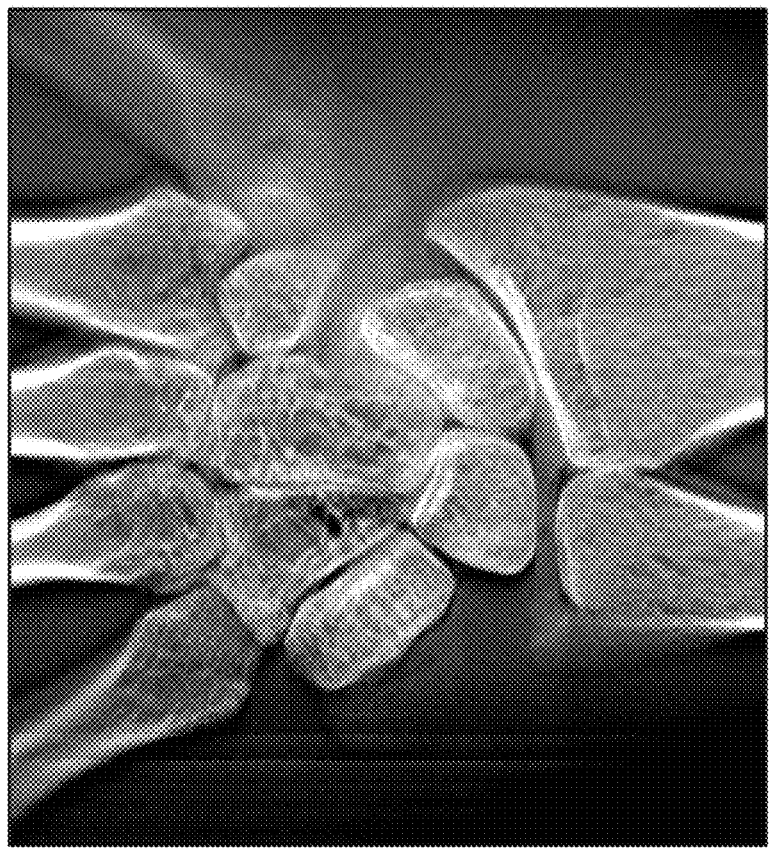

FIG. 11A and FIG. 11B illustrates another demonstration of the device of the present disclosure with two different images at different depths or heights. FIG. 11A depicts tomosynthesis reconstruction slices of a wrist from a specimen in the plane of the capitate. FIG. 11B depicts tomosynthesis reconstruction slices of the same wrist in the palmar aspect of the scaphoid and hook of the hamate.

Some of the subject matter disclosed herein can be implemented in or with software in combination with hardware and/or firmware. For example, the subject matter described herein can be implemented in software executed by a processor or processing unit. In one exemplary implementation, the subject matter described herein can be implemented using a computer readable medium having stored thereon computer executable instructions that when executed by a processor of a computer control the computer to perform steps. Exemplary computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. A compact x-ray imaging system, comprising:
an x-ray source array comprising a plurality of spatially distributed x-ray focal spots and a digital area x-ray detector;
a collimation assembly connected to an exit window of the x-ray source array configured to substantially collimate x-ray radiation generated from each of the plurality of spatially distributed x-ray focal spots to a surface of the digital area x-ray detector;
an electronic switching device comprising:
a high voltage power supply;
a current source;
a switch configured to sequentially connect the current source to a plurality of field emission cathodes of the compact x-ray imaging system, with a pre-set current value, one at a time, to produce one or more projection images for tomosynthesis reconstruction without any mechanical motion of either the x-ray source array or the digital area x-ray detector; and
a trigger comprising one or more first processors and/or circuitry configured to synchronize detector data collection with x-ray exposure from the plurality of spatially distributed x-ray focal spots; and
a mechanical support configured to enable a position and orientation of the x-ray source array and the digital area x-ray detector to be adjusted such that both upper and lower extremities of a patient can be imaged using tomosynthesis in either a non-load bearing position or a load bearing position;
wherein the compact x-ray imaging system is configured to operate in a plurality of imaging modes;
wherein, when the compact x-ray imaging system is operated in the tomosynthesis imaging mode, a scanning x-ray beam is produced by sequentially activating x-ray beams from the plurality of spatially distributed x-ray focal spots electronically without moving any of the x-ray source array, the digital area x-ray detector, or the patient, in order to collect one or more required projection images for tomosynthesis reconstruction; and
wherein, when the compact x-ray imaging system is operated in the pulsed fluoroscopy imaging mode, x-ray radiation generated from a central focal spot of the plurality of spatially distributed x-ray focal spots is pulsed from about 5 to 30 pulses per second and, for each x-ray pulse, an image of an object being scanned is formed and displayed to produce an x-ray movie of the object.

2. The compact x-ray imaging system of claim 1, wherein the x-ray imaging system is configured to be operated either in the tomosynthesis imaging mode or in the pulsed fluoroscopy mode.

3. The compact x-ray imaging system of claim 1, wherein the plurality of imaging modes comprises a stereotactic mode.

4. The compact x-ray imaging system of claim 3, wherein, when the compact x-ray imaging system is operated in the stereotactic mode, two discrete focal spots of the plurality of spatially distributed x-ray focal spots are activated to emit x-ray radiation causing two projection images to be formed and displayed from two different angles.

5. The compact x-ray imaging system of claim 1, wherein:
the collimation assembly comprises a primary collimator and a secondary collimator;
the primary collimator comprises a plurality of apertures; and
each aperture of the plurality of apertures is configured to allow radiation from one corresponding x-ray focal spot to pass through.

6. The compact x-ray imaging system of claim 1, wherein:
the x-ray source array comprises between, and including, about five and about sixty individually controllable carbon nanotube emitters as electron sources;
the x-ray source array has a unipolar design with an anode voltage between, and including, about 0 kV and 120 kV, and an x-ray tube current of between, and including, about 0.05 mA and 20 mA; and
the spatial distribution of the focal spots is a line, circle, 2D array, or any other two-dimensional (2D1) or three-dimensional (3D1 geometrical configuration.

7. The compact x-ray imaging system of claim 1, wherein at least one of the plurality of x-ray focal spots is microfocused with a spot size in a range of between, and including, about 0.01 mm and 0.3 mm.

8. The compact x-ray imaging system of claim 7, wherein the plurality of x-ray focal spots of the x-ray source array are positioned in a plane which is substantially perpendicular to a plane in which the digital area x-ray detector is positioned.

9. The compact x-ray imaging system of claim 7, wherein the plurality of x-ray focal spots of the x-ray source array are positioned in a plane that is substantially parallel to a plane in which the digital area x-ray detector is positioned.

10. The compact x-ray imaging system of claim 1, wherein the mechanical support is a mini c-arm.

11. The compact x-ray imaging system of claim 1, wherein the electronic switching device is configured to operate the high voltage power supply at more than one energy level during a single imaging sequence, such that projection images obtained at different anode energy levels can be combined to produce contrast enhanced two-dimensional (2D) radiographic images and three-dimensional (3D) tomosynthesis images.

12. The compact x-ray imaging system of claim 1, comprising one or more second processors and a non-transitory computer readable medium comprising executable instructions;
wherein the one or more second processors is configured to automatically register non load-bearing images and load-bearing images to produce load-induced structural deformation and/or displacement of the upper extremity or the lower extremity of the patient being imaged.

13. The compact x-ray imaging system of claim 1, further comprising one or more second processors and a non-transitory computer readable medium comprising executable instructions;
wherein the one or more second processors is configured to automatically register pre-contrast agent injection images and post-contrast agent injection images to produce contrast agent enhanced images of the upper extremity or the lower extremity of the patient being imaged.

14. A method of x-ray imaging using a compact x-ray imaging system, the method comprising:
providing an x-ray source array, which has a plurality of spatially distributed x-ray focal spots, and a digital area x-ray detector;
substantially collimating x-ray radiation generated from each of the plurality of spatially distributed x-ray focal spots to a surface of the digital area x-ray detector using a collimation assembly connected to an exit window of the x-ray source array;

providing an electronic switching device comprising:
  a high voltage power supply;
  a current source;
  a switch; and
  a trigger comprising one or more first processors and/or circuitry;
positioning and orienting the x-ray source array and the digital area x-ray detector such that both upper and lower extremities of a patient can be imaged using tomosynthesis in either a non-load bearing position or in a load bearing position, a relative position between the plurality of spatially distributed x-ray focal spots and the digital area x-ray detector remaining unchanged during the positioning and orienting of the x-ray source array and the digital area x-ray detector;
sequentially connecting the current source to a plurality of field emission cathodes of the compact x-ray imaging system, with a pre-set current value, one at a time, to produce one or more projection images for tomosynthesis reconstruction without any mechanical motion of either the x-ray source array or the digital area x-ray detector; and
synchronizing detector data collection with x-ray exposure from the plurality of spatially distributed x-ray focal spots;
wherein the compact x-ray imaging system is configured to operate in a plurality of imaging modes
wherein, when the compact x-ray imaging system is operated in the tomosynthesis imaging mode, a scanning x-ray beam is produced by sequentially activating x-ray beams from the plurality of spatially distributed x-ray focal spots electronically without moving any of the x-ray source array, the digital area x-ray detector, or the patient, in order to collect one or more required projection images for tomosynthesis reconstruction; and
wherein, when the compact x-ray imaging system is operated in the pulsed fluoroscopy imaging mode, x-ray radiation generated from a central focal spot of the plurality of spatially distributed x-ray focal spots is pulsed from about 5 to 30 pulses per second and, for each x-ray pulse, an image of an object being scanned is formed and displayed to produce an x-ray movie of the object.

15. A mini c-arm x-ray imaging system comprising:
a carbon nanotube based micro-focus x-ray source array comprising a plurality of spatially distributed micro-focus x-ray focal spots and a digital area x-ray detector mounted on a mini c-arm;
a collimation assembly connected to an exit window of the micro-focus x-ray source array configured to substantially collimate the x-ray radiation generated from each of the plurality of spatially distributed micro-focus x-ray focal spots to a surface of the digital area x-ray detector; and
an electronic switching device comprising:
  a high voltage power supply;
  a current source;
  a switch configured to sequentially connect the current source to a plurality of field emission cathodes of the mini c-arm x-ray imaging system with a pre-set current value, one at a time, to produce one or more projection images for tomosynthesis reconstruction without any mechanical motion of either the micro-focus x-ray source array or the digital area x-ray detector; and
  a trigger comprising one or more processors and/or circuitry configured to synchronize detector data collection with x-ray exposure from the plurality of spatially distributed micro-focus x-ray focal spots;
wherein the mini c-arm x-ray imaging system is configured to operate in a three-dimensional tomosynthesis imaging mode, a fluoroscopy mode, and a stereotactic mode.

16. A method of x-ray imaging using a mini c-arm x-ray imaging system comprising:
providing a mini c-arm x-ray imaging system comprising:
  a carbon nanotube based micro-focus x-ray source array with a plurality of spatially distributed micro-focus x-ray focal spots; and
  a digital area x-ray detector mounted on a mini c-arm;
substantially collimating x-ray radiation generated from each of the plurality of spatially distributed micro-focus x-ray focal spots to a surface of the digital area x-ray detector using a collimation assembly connected to an exit window of the micro-focus x-ray source array;
providing an electronic switching device comprising:
  a high voltage power supply;
  a current source;
  a switch; and
  a trigger comprising one or more processors and/or circuitry;
sequentially connecting the current source to a plurality of field emission cathodes of the mini c-arm x-ray imaging system with a pre-set current value, one at a time, to produce one or more projection images for tomosynthesis reconstruction without any mechanical motion of either the micro-focus x-ray source array or the digital area x-ray detector; and
synchronizing detector data collection with x-ray exposure from the plurality of spatially distributed micro-focus x-ray focal spots;
wherein the mini c-arm x-ray imaging system is configured to operate in a three-dimensional tomosynthesis imaging mode, a fluoroscopy mode, and a stereotactic mode.

* * * * *